United States Patent
Li et al.

(10) Patent No.: US 8,652,504 B2
(45) Date of Patent: Feb. 18, 2014

(54) SOLID POLYMER DELIVERY COMPOSITIONS AND METHODS FOR USE THEREOF

(75) Inventors: Hong Li, Jilin (CN); William G. Turnell, San Diego, CA (US); Yumin Yuan, San Diego, CA (US); Geoffrey C. Landis, Carlsbad, CA (US); Ryan L. Knoy, San Diego, CA (US)

(73) Assignee: Medivas, LLC, San Diego, CA (US)

( * ) Notice: Subject to any disclaimer, the term of this patent is extended or adjusted under 35 U.S.C. 154(b) by 1681 days.

(21) Appl. No.: 11/525,491

(22) Filed: Sep. 21, 2006

(65) Prior Publication Data

US 2007/0077272 A1    Apr. 5, 2007

Related U.S. Application Data

(60) Provisional application No. 60/719,809, filed on Sep. 22, 2005.

(51) Int. Cl.
*A61K 48/00* (2006.01)
*A61K 39/395* (2006.01)
*C08F 20/00* (2006.01)
*A61F 2/02* (2006.01)

(52) U.S. Cl.
USPC ........... 424/423; 424/133.1; 514/44; 525/440

(58) Field of Classification Search
None
See application file for complete search history.

(56) References Cited

U.S. PATENT DOCUMENTS

| | | | |
|---|---|---|---|
| 4,129,594 A | 12/1978 | Baker et al. | |
| 4,221,787 A | 9/1980 | Bodor et al. | |
| 4,443,563 A | 4/1984 | Dirkilov et al. | |
| 4,994,551 A | 2/1991 | Fung et al. | |
| 5,057,313 A | 10/1991 | Shih et al. | |
| 5,091,560 A | 2/1992 | Rowland | |
| 5,100,992 A | 3/1992 | Cohn et al. | |
| 5,133,742 A | 7/1992 | Pinchuk | |
| 5,206,341 A | 4/1993 | Ibay et al. | |
| 5,286,837 A | 2/1994 | Burrows et al. | |
| 5,300,114 A | 4/1994 | Gwon et al. | |

(Continued)

FOREIGN PATENT DOCUMENTS

| | | |
|---|---|---|
| AU | 2001287015 | 3/2002 |
| AU | 2006204654 | 9/2006 |

(Continued)

OTHER PUBLICATIONS

Subbiah et al, Electrospinning of Nanofibers, Feb. 15, 2005, Journal of Applied Polymer Science, vol. 96, p. 557-569.*

(Continued)

*Primary Examiner* — Ernst Arnold
*Assistant Examiner* — Jianfeng Song
(74) *Attorney, Agent, or Firm* — Nixon & Vanderhye P.C.

(57) ABSTRACT

The present invention provides an implantable solid polymer delivery composition that can be formulated to release a bioactive agent to an interior body site at a controlled rate over an extended period of time by adjusting the various components of the composition. The controlled delivery of the composition avoids an initial drug spike, resulting in a smooth delivery profile over time. Polymer layers in the composition can be porous and are both biodegradable in water and body enzymes and biocompatible. Methods of making the implantable solid polymer compositions and methods of delivering a bioactive agent at a controlled rate to an interior body site are also provided.

15 Claims, 3 Drawing Sheets

Carrier Layer (black): biodegradable, biocompatible polymer of general formula (I) or (III) matrixed with bioactive molecule Barrier Layers (grey)

Coating Layers (white)

(56) References Cited

U.S. PATENT DOCUMENTS

| | | | |
|---|---|---|---|
| 5,449,513 A | 9/1995 | Yokoyama et al. | |
| 5,482,700 A | 1/1996 | Deutsch et al. | |
| 5,485,496 A | 1/1996 | Lee et al. | |
| 5,514,379 A | 5/1996 | Weissleder et al. | |
| 5,516,881 A | 5/1996 | Lee et al. | |
| 5,554,692 A | 9/1996 | Ross | |
| 5,583,206 A | 12/1996 | Snow et al. | |
| 5,591,227 A | 1/1997 | Dinh et al. | |
| 5,610,241 A | 3/1997 | Lee et al. | |
| 5,653,998 A | 8/1997 | Hamann et al. | |
| 5,721,131 A | 2/1998 | Rudolph et al. | |
| 5,753,234 A | 5/1998 | Lee et al. | |
| 5,762,939 A | 6/1998 | Smith et al. | |
| 5,770,229 A | 6/1998 | Tanihara et al. | |
| 5,849,841 A | 12/1998 | Muhlebach et al. | |
| 5,852,155 A | 12/1998 | Bussink et al. | |
| 5,858,368 A | 1/1999 | Smith et al. | |
| 5,861,387 A | 1/1999 | Labrie et al. | |
| 5,874,064 A | 2/1999 | Edwards et al. | |
| 5,882,679 A | 3/1999 | Needham | |
| 5,885,491 A | 3/1999 | Valdivia et al. | |
| 5,904,936 A | 5/1999 | Huille et al. | |
| 5,906,934 A | 5/1999 | Grande et al. | |
| 5,916,585 A | 6/1999 | Cook et al. | |
| 5,919,893 A | 7/1999 | Roby et al. | |
| 5,929,893 A | 7/1999 | Son et al. | |
| 5,968,794 A | 10/1999 | Samain et al. | |
| 5,972,027 A | 10/1999 | Johnson | |
| 6,004,573 A | 12/1999 | Rathi et al. | |
| 6,103,526 A | 8/2000 | Smith et al. | |
| 6,111,058 A | 8/2000 | Warzelhan et al. | |
| 6,153,252 A * | 11/2000 | Hossainy et al. | 427/2.3 |
| 6,171,610 B1 | 1/2001 | Vacanti et al. | |
| 6,210,441 B1 | 4/2001 | Flodin | |
| 6,221,997 B1 * | 4/2001 | Woodhouse et al. | 528/61 |
| 6,228,391 B1 | 5/2001 | Shimizu et al. | |
| 6,245,532 B1 | 6/2001 | Smith et al. | |
| 6,299,597 B1 | 10/2001 | Buscemi et al. | |
| 6,342,300 B1 | 1/2002 | Bengs et al. | |
| 6,352,667 B1 | 3/2002 | English | |
| 6,365,160 B1 | 4/2002 | Webb et al. | |
| 6,428,807 B1 | 8/2002 | MacFarlan et al. | |
| 6,476,204 B1 | 11/2002 | Kim et al. | |
| 6,503,538 B1 * | 1/2003 | Chu et al. | 424/497 |
| 6,521,431 B1 | 2/2003 | Kiser et al. | |
| 6,541,606 B2 | 4/2003 | Margolin et al. | |
| 6,660,525 B2 | 12/2003 | Martin et al. | |
| 6,703,040 B2 | 3/2004 | Katsarava et al. | |
| 6,716,445 B2 | 4/2004 | Won et al. | |
| 6,793,938 B2 | 9/2004 | Sankaram | |
| 6,830,747 B2 | 12/2004 | Lang et al. | |
| 6,982,249 B1 | 1/2006 | Schmaier et al. | |
| 6,984,393 B2 | 1/2006 | Amsden | |
| 6,994,867 B1 | 2/2006 | Hossainy et al. | |
| 7,026,156 B1 | 4/2006 | Clark et al. | |
| 7,041,785 B1 | 5/2006 | Recoli et al. | |
| 7,122,202 B2 | 10/2006 | Allen et al. | |
| 7,220,816 B2 | 5/2007 | Pacetti et al. | |
| 7,304,122 B2 | 12/2007 | Chu et al. | |
| 7,408,018 B2 | 8/2008 | Chu et al. | |
| 7,538,180 B2 | 5/2009 | Pacetti et al. | |
| 7,649,022 B2 | 1/2010 | Gomurashvili et al. | |
| 7,658,727 B1 | 2/2010 | Fernandes et al. | |
| 7,670,829 B2 | 3/2010 | Spagnoli et al. | |
| 7,744,861 B2 | 6/2010 | Zhao et al. | |
| 7,785,618 B2 | 8/2010 | Elmaleh et al. | |
| 7,794,494 B2 | 9/2010 | Sahatjian et al. | |
| 7,794,706 B2 | 9/2010 | Carpenter et al. | |
| 7,863,406 B2 | 1/2011 | Chu et al. | |
| 7,935,493 B2 | 5/2011 | Michnick et al. | |
| 8,067,031 B2 | 11/2011 | Daniloff et al. | |
| 8,163,269 B2 | 4/2012 | Carpenter et al. | |
| 2001/0038851 A1 | 11/2001 | Allen et al. | |
| 2002/0015720 A1 | 2/2002 | Katsarava et al. | |
| 2002/0034532 A1 | 3/2002 | Broadbeck et al. | |
| 2002/0044972 A1 | 4/2002 | Davis et al. | |
| 2002/0049495 A1 | 4/2002 | Kutryk et al. | |
| 2002/0106369 A1 | 8/2002 | Horvath et al. | |
| 2002/0164374 A1 | 11/2002 | Jackson et al. | |
| 2002/0165347 A1 | 11/2002 | Fox et al. | |
| 2002/0168338 A1 | 11/2002 | Baird | |
| 2002/0173586 A1 | 11/2002 | Jeong et al. | |
| 2003/0064053 A1 | 4/2003 | Liu et al. | |
| 2003/0130185 A1 | 7/2003 | Bar-Or et al. | |
| 2003/0175239 A1 | 9/2003 | Margolin et al. | |
| 2003/0215454 A1 | 11/2003 | Colb et al. | |
| 2003/0217748 A1 | 11/2003 | Giroux | |
| 2003/0229393 A1 | 12/2003 | Kutryk et al. | |
| 2004/0017387 A1 | 1/2004 | Soltero et al. | |
| 2004/0024069 A1 | 2/2004 | Chen et al. | |
| 2004/0057958 A1 | 3/2004 | Waggoner et al. | |
| 2004/0110285 A1 | 6/2004 | Lendlein et al. | |
| 2004/0170685 A1 | 9/2004 | Carpenter et al. | |
| 2004/0213759 A1 | 10/2004 | Zalipsky et al. | |
| 2004/0213766 A1 | 10/2004 | Francois | |
| 2004/0253293 A1 | 12/2004 | Shafiee et al. | |
| 2004/0254151 A1 | 12/2004 | Ralston et al. | |
| 2004/0258702 A1 | 12/2004 | Blonder et al. | |
| 2005/0013812 A1 | 1/2005 | Dow et al. | |
| 2005/0019366 A1 | 1/2005 | Zeldis | |
| 2005/0019404 A1 | 1/2005 | Sung et al. | |
| 2005/0025752 A1 | 2/2005 | Kutryk et al. | |
| 2005/0043787 A1 | 2/2005 | Kutryk et al. | |
| 2005/0053667 A1 | 3/2005 | Irvine et al. | |
| 2005/0064602 A1 | 3/2005 | Kaufman et al. | |
| 2005/0175583 A1 | 8/2005 | Tamarkin et al. | |
| 2005/0208091 A1 | 9/2005 | Pacetti | |
| 2005/0238689 A1 | 10/2005 | Carpenter et al. | |
| 2005/0245637 A1 | 11/2005 | Hossainy et al. | |
| 2005/0260259 A1 | 11/2005 | Bolotin | |
| 2005/0265960 A1 | 12/2005 | Pacetti et al. | |
| 2005/0271700 A1 | 12/2005 | DesNoyer et al. | |
| 2005/0271701 A1 | 12/2005 | Cottone, Jr. et al. | |
| 2005/0287184 A1 | 12/2005 | Hossainy et al. | |
| 2005/0288481 A1 | 12/2005 | DesNoyer et al. | |
| 2006/0002947 A1 | 1/2006 | Humphreys et al. | |
| 2006/0008532 A1 | 1/2006 | Govardhan et al. | |
| 2006/0009498 A1 | 1/2006 | Whitcup | |
| 2006/0013855 A1 | 1/2006 | Carpenter et al. | |
| 2006/0024357 A1 | 2/2006 | Carpenter et al. | |
| 2006/0036311 A1 | 2/2006 | Nakayama et al. | |
| 2006/0074191 A1 | 4/2006 | DesNoyer et al. | |
| 2006/0111546 A1 | 5/2006 | Pacetti et al. | |
| 2006/0115455 A1 | 6/2006 | Reed et al. | |
| 2006/0121012 A1 | 6/2006 | Kutryk et al. | |
| 2006/0135476 A1 | 6/2006 | Kutryk et al. | |
| 2006/0177416 A1 | 8/2006 | Turnell et al. | |
| 2006/0188469 A1 | 8/2006 | Turnell et al. | |
| 2006/0188486 A1 | 8/2006 | Carpenter et al. | |
| 2006/0224331 A1 | 10/2006 | Watson Michnick et al. | |
| 2006/0286064 A1 | 12/2006 | Turnell et al. | |
| 2007/0042017 A1 | 2/2007 | Kutryk et al. | |
| 2007/0055367 A1 | 3/2007 | Kutryk et al. | |
| 2007/0066541 A1 | 3/2007 | Hughes et al. | |
| 2007/0071790 A1 | 3/2007 | Ameer et al. | |
| 2007/0106035 A1 | 5/2007 | Gomurashvili et al. | |
| 2007/0128250 A1 | 6/2007 | Katsarava et al. | |
| 2007/0134332 A1 | 6/2007 | Turnell et al. | |
| 2007/0141100 A1 | 6/2007 | Sung et al. | |
| 2007/0141107 A1 | 6/2007 | Kutryk et al. | |
| 2007/0156232 A1 | 7/2007 | Kutryk et al. | |
| 2007/0160622 A1 | 7/2007 | Turnell et al. | |
| 2007/0167605 A1 | 7/2007 | Chu et al. | |
| 2007/0191932 A1 | 8/2007 | Kutryk et al. | |
| 2007/0196422 A1 | 8/2007 | Kutryk et al. | |
| 2007/0213801 A1 | 9/2007 | Kutryk et al. | |
| 2007/0282011 A1 | 12/2007 | Gomurashvili et al. | |
| 2007/0287987 A1 | 12/2007 | Katsarava et al. | |
| 2007/0292476 A1 | 12/2007 | Landis et al. | |
| 2007/0299155 A1 | 12/2007 | Carpenter et al. | |
| 2008/0020015 A1 | 1/2008 | Carpenter et al. | |
| 2008/0050419 A1 | 2/2008 | Katsarava et al. | |
| 2008/0160089 A1 | 7/2008 | Vitiello et al. | |
| 2008/0288057 A1 | 11/2008 | Carpenter et al. | |

(56) References Cited

U.S. PATENT DOCUMENTS

| | | | |
|---|---|---|---|
| 2008/0299174 A1 | 12/2008 | Gomurashvili et al. | |
| 2009/0022772 A1 | 1/2009 | Carpenter et al. | |
| 2009/0029937 A1 | 1/2009 | Chu et al. | |
| 2009/0068743 A1 | 3/2009 | Turnell et al. | |
| 2009/0202620 A1 | 8/2009 | Turnell et al. | |
| 2009/0238854 A1 | 9/2009 | Pacetti et al. | |
| 2010/0004390 A1 | 1/2010 | Turnell et al. | |
| 2010/0040664 A1 | 2/2010 | Katsarava et al. | |
| 2011/0027379 A1 | 2/2011 | Chu et al. | |
| 2011/0137406 A1 | 6/2011 | Carpenter et al. | |
| 2012/0027859 A1 | 2/2012 | Turnell et al. | |
| 2012/0328706 A1 | 12/2012 | Turnell et al. | |

FOREIGN PATENT DOCUMENTS

| | | | |
|---|---|---|---|
| CA | 2225792 | 11/1997 | |
| CA | 2419429 | 7/2010 | |
| CN | 1281355 | 1/2001 | |
| CN | 1296852 | 5/2001 | |
| DE | 42 24 401 | 1/1994 | |
| EP | 0 147 780 | * 7/1985 | |
| EP | 0 396 429 | 11/1990 | |
| EP | 0447719 | 9/1991 | |
| EP | 0932399 | 1/2006 | |
| EP | 1 313 794 | 11/2006 | |
| EP | 1 848 410 | 10/2007 | |
| EP | 1 933 881 | 6/2008 | |
| EP | 1 945 682 | 7/2008 | |
| EP | 2 185 626 | 5/2010 | |
| JP | 05-084259 | 4/1993 | |
| JP | 06-211648 | 8/1994 | |
| JP | 2002-537415 | 11/2002 | |
| JP | 2003-519650 | 6/2003 | |
| JP | 2003-519651 | 6/2003 | |
| JP | 2003-534360 | 11/2003 | |
| JP | 2004-502720 | 1/2004 | |
| JP | 2004-507600 | 3/2004 | |
| JP | 2004-513872 | 5/2004 | |
| JP | 2005-504797 | 2/2005 | |
| JP | 2006-504991 | 2/2006 | |
| JP | 2007-513741 | 5/2007 | |
| JP | 2008-530206 | 8/2008 | |
| SU | 872531 | 10/1981 | |
| SU | 876663 | 10/1981 | |
| SU | 905228 | 2/1982 | |
| SU | 790725 | 2/1983 | |
| SU | 1016314 | 5/1983 | |
| SU | 811750 | 9/1983 | |
| SU | 1293518 | 2/1987 | |
| WO | 94/04642 | 3/1994 | |
| WO | 97/30104 | 8/1997 | |
| WO | 98/32398 | 7/1998 | |
| WO | 99/58151 | 11/1999 | |
| WO | 99/61916 | 12/1999 | |
| WO | 01/28591 | 4/2001 | |
| WO | 01/51027 | 7/2001 | |
| WO | 01/91703 | 12/2001 | |
| WO | 02/18477 | 3/2002 | |
| WO | 03/024420 | 3/2003 | |
| WO | 03/062298 | 7/2003 | |
| WO | 2004/039944 | 5/2004 | |
| WO | 2004/040339 | 5/2004 | |
| WO | 2005/027906 | 3/2005 | |
| WO | 2005/061024 | 7/2005 | |
| WO | 2005/097186 | 10/2005 | |
| WO | 2005/112587 | 12/2005 | |
| WO | 2005/112884 | 12/2005 | |
| WO | 2005/118681 | 12/2005 | |
| WO | 2006/050091 | 5/2006 | |
| WO | 2006/083874 | 8/2006 | |
| WO | 2006/088647 | 8/2006 | |
| WO | 2006/108167 | 10/2006 | |
| WO | 2007/035938 | 3/2007 | |
| WO | 2007/038246 | 4/2007 | |
| WO | 2007/067744 | 6/2007 | |
| WO | 2007/089870 | 8/2007 | |
| WO | 2007/133616 | 11/2007 | |
| WO | 2009/015143 | 1/2009 | |
| WO | 2009/026543 | 2/2009 | |
| WO | 2010/045241 | 4/2010 | |

OTHER PUBLICATIONS

Kartvelishvili et al., "Amino acid based bioanalogous polymers. Novel regular poly(ester urethane)s and poly(ester urea)s based on bis(L-phenylalanine) α, ω-alkylene diesters", *Macromol. Chem. Phys.*, 198:1921-1932 (1997).

Yokoe et al. "Biodegradable Polymers Based on renewable Resources. VII. Novel Random and Alternating Copolycarbonates from 1,4:3,6-Dianhydrohexitols and Aliphatic Diols", *Journal of Polymer Science: Part A: Polymer Chemistry*, 41:2312-2321 (2003).

Notice of Reasons for Rejection issued in JP 2008-532486, dated Nov. 16, 2011.

Notice of Reasons for Rejection issued in JP 2008-532405, dated Apr. 20, 2012.

Notice of Reasons for Rejection issued in JP 2009-509693, dated Aug. 17, 2012.

Supplementary European Search Report issued in EP 07 77 6644, dated Jan. 31, 2013.

Arabuli et al., "Heterochain Polymers based on Natural Amino Acids. Synthesis and Enzymatic Hydrolysis of Regular Pol(Ester Amide)S Based on Bis(L-Phenylalanine)Alpha,Omega-Alkylene Diesters and Adipic Acid", *Macromolecular Chemistry and Physics*, 195(6):2279-2289 (1994).

Arote et al., "A biodegradable poly(ester amine) based on polycaprolactone and polyethylenimine as a gene carrier", *Biomaterials*, 28(4) (2007).

Arsalani et al; "Synthesis and Characterization of Watersoluble and Carboxy-functional Polyester and Polyamide Based on Ethylenediamine-tetraacetic Acid and Their Metal Complexes", *Iranian Polymer Journal*, 12:291-296 (2003).

Asin et al., "Sequential Poly(ester amide)s Based on Glycine, Diols, and Dicarboxylic Acids: Thermal Polyesterification versus Interfacial Polyamidation. Characterization of Polymers Containing Stiff Units," *J. Polym. Sci. Part A: Polym. Chem.*, 39(24):4283-4293, (2001).

Bakker-Woudenberg et al., "Improved Efficacy of Ciprofloxacin Administered in Polyethylene Glycol-Coated Liposomes for Treatment of *Klebsiella pneumoniae* Pneumonia in Rats", *Antimicrobial Agents*, 45:1487 (2001).

Becker et al., "Prevention of Postoperative Abdominal Adhesions by a Sodium Hyaluronate-Based Bioresorbable Membrane: A Prospective, Randomized, Double-Blind Multicenter Study", *J Am Coll. Surg.*, 183:297-306 (1996).

Chunmeng et al., "Effects of Dermal Multipotent Cell Transplantation on Skin Wound Healing", *Journal of Surgical Research*, 121:13-19 (2004).

Cohen et al., "Acid-Catalyzed Amide Hydrolysis Assisted by a Neighboring Amide Group", *J. Am. Chem. Soc.*, 86:5611 (1964).

De Simone et al., "Synthesis, Characterization, and Degradation of Block Polyesteramides Containing Poly (L-Lactide) Segments", *Journal of Applied Polymer Science*, 46:1813-1820 (1992).

Duncan et al, "Polymer-Drug conjugates: Towards a novel approach for the treatment of endocrine related cancer," *Endocrine Related Cancer*, 12(1) S189 (2005).

Ferns et al., "Inhibition of Neointimal Smooth Muscle Accumulation After Angioplasty by an Antibody to PDGF", *Science*, 253:1129-1132 (1991).

Fujimaki, "Processability and properties of aliphatic polyesters, 'BIONOLLE', synthesized by polycondensation reaction", *Polym. Degrad. Stabil.*, 59:209-214 (1998).

Furchgott and Zawadzki, "The obligatory role of endothelial cells in the relaxation of arterial smooth muscle by acetylcholine", *Nature*, 288:373-376 (1980).

Gabor et al., "Ketoprofen-poly(D,L-lactic-co-glycolic acid) microspheres: influence of manufacturing parameters and type of polymer on the release characteristics", *J. Microencapsulation*, 16(1):1-12 (1999).

(56) References Cited

OTHER PUBLICATIONS

Garg and Hassid, "Nitric Oxide-generating Vasodilators and 8-Bromo-Cyclic Guanosine Monophosphate Inhibit Mitogenesis and Proliferation of Cultured Rat Vascular Smooth Muscle Cells", *J Clin. Invest.*, 83:1774-1777 (1989).

Gehling et al., "In vitro differentiation of endothelial cells from AC133-positive progenitor cells", *Blood*, 95(10):3106-3112 (2000).

Gelder et al., "Human CD4+ T-cell repertoire of responses to influenza A virus hemagglutinin after recent natural infection", *J. of Virology*, 69(12):7497-7506 (1995).

Gill al., "Vascular Trauma Induces Rapid but Transient Mobilization of VEGFR2$^+$ AC133$^+$ Endothelial Precursor Cells", *Circulation Research*, 88:167-174 (2001).

Gomurashvili et al., "Amino Acid Based Bioanalogous Polymers. Synthesis and Study of New Poly(Ester Amide)S Composed of Hydrophobic α-Amino Acids and Dianhydrohexitoles", *J.M.S.—Pure Appl. Chem.*, A37(3):215-227 (2000).

Gomurashvili et al., "From Drug-Eluting Stents to Biopharmaceuticals: Poly(ester amide) a Versatile New Bioabsorbable Biopolymer. In: Polymers for Biomedical Applications", *ACS Symposium Series; American Chemical Society*, Chapter 2, pp. 10-26 (2008).

Guo et al., "Synthesis and Characterization of Novel Biodegradable Unsaturated Poly(ester amide)s", *Journal of Polymer Science: Part A: Polymer Chemistry*, 43(17):1463-1477 (2005).

Guo et al., "Synthesis and Characterization of Novel Biodegradable Unsaturated Poly(ester amide)/Poly(ethylene glycol) Diacrylate Hydrogels", *Journal of Polymer Science: Part A: Polymer Chemistry*, 43:3932-3944 (2005).

Hermann et al., "Somatostatin containing biodegradable microspheres prepared by a modified solvent evaporation method based on W/O/W-multiple emulsions", International Journal of Pharmaceutics, 126:129-138 (1995).

Hristov et al., "Endothelial Progenitor Cells, Mobilization, Differentiation, and Homing", *Arterioscler Thromb Vasc Bioi.*, 23:1185-1189 (2003).

Huang et al., "Biodegradable Polymers: Chymotrypsin Degradationi of a Low Molecular Weight Poly(ester-Urea) Containing Phenylalanine", *J Appl. Polym.Sci*, 23:429-437 (1979).

Imai, Y., "Poly-2.6-piperazinedione: A New Class of Polymer Derived from N.N.N'.N'-Ethylenediaminetetraacetic Acid Dianhydride and Diamines", *Die Makromolekulare Chemie*, 138(3472)293-297 (1970).

Itaka et al., "Supramolecular nanocarrier of siRNA from PEG-based block catiomer carrying diamine side chain with distrinctive pKa directed to enhance intracellular gene silencing", *Journal of American Chemical Society*, 126:13612-13613 (2004).

Janssen et al., "Histidine Tagging Both Allows Convenient Single-step Purification of Bovine Rhodopsin and Exerts Ionic Strength-dependent Effects on Its Photochemistry", *Journal of Biological Chemistry*, 270(19):11222-11229 (1995).

Katas et al., "Development and characterization of chitosan nanoparticles for siRNA delivery", *Journal of Controlled Release*, 115:216-225 (2006).

Katsarava et al., "Synthesis of high-molecular-weight polysuccinamides by polycondensation of active succinates with diamines", *Makromol. Chem. B.*, 187:2053 (1986).

Kim et al., "Preparation of Multi vesicular Liposomes", *Biochim. Biophys. Acta*, 728:339-348 (1983).

Kopecek, "The Potential of Water-Soluble Polymeric Carriers in Targeted and Site-Specific Drug Delivery," *Journal of Controlled Release*, 11:279-290 (1990).

Kühnl et al.,"C-type peptide inhibitis constrictive remodeling without compromising re-endothelialization in balloon-dilated renal arteries", *J. Endovasc. Ther.*,12:171-182 (2005).

Lee et al., "Activation of anti-hepatitis C virus responses via Toll-like receptor 7", *PNAS*, 103(6):1828-1833 (2006).

Luo and Prestwich, "Synthesis and Selective Cytotoxicity of a Hyaluronic Acid-Antitumor Bioconjugate," *Bioconjugate Chem.*, 10:755-763 (1999).

Maeda et al; "Synthesis and Properties of Superconductors Prepared from Ethylenediaminetetraacetic Acid (EDTA)—Ethylenediamine (ED) Polyamide YBC Chelate", *Journal of Polymer Science: Part A: Polymer Chemistry*, 32:1729-1738 (1994).

Maines et al., "Avian influenza (H5N1) viruses isolated from humans in Asia in 2004 exhibit increased virulence in mammals", *Journal of Virology*, 79(18):11788-11800 (2005).

Mehvar, "Modulation of the Pharmacokinetics and Pharmacodynamics of Proteins by Polyethylene Glycol Conjugation," *J Pharm. Pharmaceut. Sci.*, 31(1):125-136, (2000).

Mitchell et al., "Polyarginine enters cells more efficiently than other polycationic homopolymers", *The Journal of Peptide Research*, 56:318-325 (2000).

Moncada et al., "Nitric Oxide: Physiology, Pathophysiology, and Pharmacology", *Pharmacological Reviews*, 43(2):109-142 (1991).

Mu et al., "A novel controlled release formulation for the anticancer drug paclitaxel (Taxol®): PLGA nanoparticles containing vitamin E TPGS", *Journal of Controlled Release*,86:33-48 (2003).

Myers et al., "Vasorelaxant properties of the endothelium-derived relaxing factor more closely resemble S-nitrosocysteine than nitric oxide", *Nature*, 345:161-163 (1990).

Okada et al., "Biodegradable Polymers Based on Renewable Resources: Polyesters Composed of 1,4:3,6-Dianhydrohexitol and Aliphatic Dicarboxylic Acid Units", *Journal of Applied Polymer Science*, 62:2257-2265 (1996).

Okada et al., "Biodegradable Polymers Based on Renewable Resources: V. Synthesis and Biodegradation Behavior of Poly(esteramide)s Composed of 1,4:3,6-Dianhydro-D-glucitol, a-Amino Acid, and Aliphatic Dicarboxylic Acid Units", *Journal of Applied Polymer Science*, 81:2721-2734 (2001).

Peichev et al., "Expression of VEGFR-2 and AC133 by circulating human CD34+ cells identifies a population of functional endothelial precursors", *Blood*, 95(3):952-958 (2000).

Poznansky and Juliano, "Biological Approaches to the Controlled Delivery of Drugs: A Critical Review", *Pharmacal. Rev.*, 36:277-236 (1984).

Qian et al., "Perparation of biodegradable polyesteramide microspheres", *Colloid Polym Sci*, 282:1083-1088 (2004).

Quaglia et al., "New segmented copolymers containing poly(e-caprolactone) and etheramide segments for the controlled release of bioactive compounds", *Journal of Controlled Release*, 83:263-271 (2002).

Radomski et al., "Comparative pharmacology of endothelium-derived relaxing factor, nitric oxide and prostacyclin in platelets", *Br. J Pharmac.*, 92:181-187 (1987).

Ratnala et al., "Large-scale Overproduction, Functional Purification and Ligand Affinities of the His-Tagged Human Histamine H1 Receptor", *Eur. J. Biochem*, 271:2636-2646 (2004).

Reddy et al., "In vivo Cytotoxic T Lymphocyte Induction with Soluble Proteins Administered in Liposomes", *J lmmunol.*, 148:1585 (1992).

Rock, "A new foreign policy: MHC class I molecules monitor the outside world", *Immunol. Today*, 17:131 (1996).

Rosca et al., "Microparticle formation and its mechanism in single and double emulsion solvent evaporation", *Journal of Controlled Release*, 99:271-280 (2004).

Saotome. et al., "Novel Enzymatically Degradable Polymers Comprising a-Amino Acid, 1,2-Ethanediol, and Adipic Acid", *Chemistry Letters*, pp. 21-24 (1991 ).

Schickli et al., "Plasmid-only rescue of influenza A virus vaccine candidates", *Philosophical Transactions of the Royal Society*, 356(1416):1965-1973 (2001).

Schofield et al., "The Effect of a α4β1-Integrin Binding Sequences of Fibronectin on Growth of Cells From Human Hematopoietic Progenitors", *Blood*, 91(9):3230-3238 (1998).

Shirahama et al., "Synthesis and Enzymatic Degradation of High Molecular Weight Aliphatic Polyesters",*J. Appl. Polym. Sci.*, 80:340-347 (2001).

Stiborova et al., "One-Step Metal-Affinity Purificaiton of Histidine-Tagged Proteins by Temperature-Triggered Precipitation", *Biotechnology and Bioengineering*, 82(5):605-611 (2003).

Subbiah et al., "Electrospinning of Nanofibers", *Journal of Applied Polymer Science*, 96:557-569 (2005).

(56) References Cited

OTHER PUBLICATIONS

Szoka et al., "Comparative Properties and Methods of Preparation of Lipid Vesicles (Liposomes)", *Ann. Rev. Biophys. Bioeng.*, 9:467-508 (1980).

Tarvainen et al., "Degradation of and drug release from a novel 2,2-bis(2-oxazoline) linked poly(lactic acid) polymer", Journal of Controlled Release, 81:251-261 (2002).

Tulu et al; "Synthesis and properties of hydrophilic polymers. Part 7. Preparation, characterization and metal complexation of carboxy-functional polyesters based on poly(ethylene glycol)", *Polymer International*, 48:909-914 (1999).

Urbich and Dimmeler, "Endothelial Progenitor Cells Characterization and Role in Vascular Biology", *Circulation Research*, 95:343-353 (2004).

Vigneron et al., "Etude Cinetique de L'hydrolyse des Amides Aliphatiques", *Bull. Soc. Chim. Belg.*, 69:616 (1960).

Webb et al., "Preclinical pharmacology, toxicology and efficacy of sphingomyelin/cholesterolliposomal vincristine for therapeutic treatment of cancer", *Cancer Chemotherapy and Pharmacology*, 42:461 (1998).

Xing et al., *Journal of Controlled Release*, 93:293-300 (2003).

Xu et al., "Designer Glycopeptides for Cytotoxic T Cell-based Elimination of Carcinomas", *Journal of Experimental Medicine*, 199(5):707-716 (2004).

Yamaguchi et al., "Bone marrow cells differentiate into wound myofibroblasts and accelerate the healing of wounds with exposed bones when combined with an occlusive dressing", *British Journal of Dermatology*, 152:616-622 (2005).

Yang et al., "Positively charged polyethylenimines enhance nasal absorption of the negatively charged drug, low molecular weight heparin", *Journal of Controlled Release*, 115:289-297 (2006).

\* cited by examiner

SOLID POLYMER DELIVERY COMPOSITIONS AND METHODS FOR USE THEREOF

RELATED APPLICATION

This application relies for priority under 35 U.S.C. §119(e) on U.S. Ser. No. 60/719,809, filed Sep. 22, 2005 which is incorporated herein by reference.

FIELD OF THE INVENTION

The invention relates generally to drug-eluting implantable polymer compositions and in particular to biodegradable, biocompatible solid polymer delivery compositions for insertion at surgical sites.

BACKGROUND INFORMATION

Systemic delivery of pharmacologically active agents, including by inhalation parenteral, topical, or transdermal delivery or by ingestion, is an effective and easily managed mode of administration, but is less than adequate for some treatment applications. For example, some pharmacologically active agents are poorly absorbed from the blood stream, or alternatively, irritate the stomach lining. Thus, in some instances, local delivery of pharmacologically active agents is desirable.

Local delivery of pharmacologically active agents to peripheral nerves is often times desirable for the management of acute and chronic pain. However, local delivery of pharmacologically active agents to peripheral nerves is currently primarily performed by bolus injections or by the insertion of an infusion catheter. For example, bupivacaine infusion has been used to alleviate pain at iliac crest donor sites (Wilkes R A. and Thomas W G. (1994) *Journal of Bone & Joint Surgery—British Volume.* 76(3):503). Chronic epidural bupivacaine-opioid infusion has also been used to treat intractable cancer pain (Du Pen S L. et al., *Pain* (1992) 51(2):263-4).

The treatment of chronic osteomyelitis includes systemic antibiotics. However, the delivery of antibiotics to bone varies considerably. Oral antibiotics are unpredictable for this use, effect relatively low levels of bone, and are infrequently used. Intravenous antibiotics are used commonly in the treatment of chronic osteomyelitis, but six weeks of intravenous antibiotics is necessary for adequate therapy. Even with prolonged intravenous antibiotics, there is a significant relapse rate.

Although bolus injections and infusions are generally a safe and efficacious form of treatment, this mode of local delivery can be limited by the volume of liquid that can be injected, the maximal non-toxic concentration of the pharmacologically active agent that can be administered, and the system toxicity levels that can ensue subsequent to absorption and circulation to other body organs. In addition, bolus infusions are not always effective. For example, in one study intra-articular bupivacaine (up to 0.5%) at a rate of 4 mL/hr following primary total knee arthroplasty neither reduced morphine requirements nor decreased subjective pain scores during the first 24 hours after surgery. The lack of effective pain control with intra-articular bupivacaine infusion was speculated to result from the difficulty in providing effective local anesthetic effect in the relatively large intra-articular space without drug overdose. One patient in the reported study receiving 0.5% intra-articular bupivacaine at 4 mL/hr had a serum bupivacaine level of 1.2 µg/mL, in excess of the 1.0 µg/mL value at which toxicity has been reported (*Journal of Orthopaedic Surgery*(2002) 10(1): 53-60).

Furthermore, if administered by infusion catheter, bolus delivery requires monitoring to initially place the catheter, and continually thereafter to ensure that the catheter does not migrate. This mode of local delivery is also suboptimal. Thus, alternative methods of localized drug delivery would be desirable.

In efforts to address this need, many implantable drug delivery devices have been developed over the past several years. Such drug delivery devices may be formulated from synthetic or natural, biodegradable or non-biodegradable, polymers. Biodegradable polymers are preferred since these materials gradually degrade in vivo over time, e.g., by enzymatic or non-enzymatic hydrolysis, when placed in an aqueous, physiological environment. Thus, the use of biodegradable polymers in drug delivery devices is preferred since their use avoids the necessary removal of the drug delivery device at the end of the drug release period.

The drug is generally incorporated into the polymeric composition and formed into the desired shape outside the body. This solid implant is then typically inserted into the body of a human, animal, bird, and the like through an incision. Alternatively, small discrete particles composed of these polymers can be injected into the body by a syringe.

Certain formulations of these polymers also can be injected via syringe as a liquid polymeric composition. These compositions are administered to the body in a liquid state or, alternatively, as a solution with solid microparticles of polymer dispersed therein. Once in the body, the composition coagulates into a solid. One type of polymeric composition includes a nonreactive thermoplastic polymer or copolymer dissolved in a body fluid-dispersible solvent. This polymeric solution is placed into the body where the polymer congeals or precipitatively solidifies upon dissipation or diffusion of the solvent into the surrounding body tissues.

Non-toxic hydrogel-forming polymeric materials, which are capable of absorbing a substantial amount of water to form elastic or inelastic gels, also have been used in the formulation of drug delivery devices. See, e.g., Lee, J. (1985) *Controlled Release* 2: 277. Drug delivery devices incorporating hydrogel-forming polymers offer the flexibility of being implantable in liquid or gelled form. Once implanted, the hydrogel forming polymer absorbs water and swells. The release of a pharmacologically active agent incorporated into the device takes place through this gelled matrix via a diffusion mechanism.

However, many hydrogels, although biocompatible, are not biodegradable. Furthermore, drug delivery devices comprising hydrogels may require the use of undesirable organic solvents for their manufacture. Residual amounts of such solvents could potentially remain in the drug delivery device, where they could cause solvent-induced toxicity in surrounding tissues or cause structural or pharmacological degradation to the pharmacologically active agents incorporated within the drug delivery device.

In particular, nonbiodegradable polymer implants, most commonly various derivatives and co-polymers of poly(methylmethacrylate) and poly(N-alkyl acrylamide), have been used for local delivery of antibiotics, such as Tobramycin, gentamicin, and vancomycin. A biodegradable antibiotic implant made of polylactic acid and poly(DL-lactide):co-glycolide combined with vancomycin has been developed and evaluated in a localized osteomyelitic rabbit model (Cahoun J H et al. *Clinical Orthopaedics & Related Research. Current Trends in the Management of Disorders of the Joints.* (1997) 341:206-214). More recently the GLIADEL® wafer (Guilford Pharmaceutical Corp, Baltimore, Md.), which was FDA-approved for implant in post surgical treatment of certain kinds of brain tumors, is used to deliver an oncolytic agent, carmustine, from a wafer of a biodegradable polyanhydride copolymer. Local drug delivery from implants provides the advantage of high tissue concentrations with relatively low serum levels, thereby avoiding some of the toxicity associated with systemic delivery. Bioactive agent-impregnated polymer implants are particularly attractive because they not only deliver high tissue levels of antibiotic or oncolytic agent, but also help fill the dead space that occurs after certain surgeries.

However, drug release characteristics of such implanted drug delivery devices may be suboptimal. Many times, the release of pharmacologically active agents from an implanted drug delivery device is irregular. There is an initial burst period when the drug is released primarily from the surface of the device, followed by a second period during which little or no drug is released, and a third period during which most of the remainder of the drug is released at a substantially lower rate than in the initial burst.

Thus, despite advancements in the art, new and better drug delivery devices are needed for sustained, controlled local delivery of pharmacologically active agents that are also biodegradable and biocompatible, as well as resorbable such that removal of the device is not necessary.

SUMMARY OF THE INVENTION

In one embodiment, the invention provides a solid polymer delivery composition having a biodegradable, biocompatible

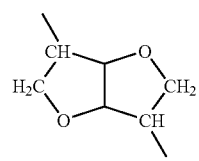

Formula (II)

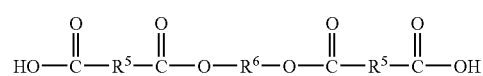

Formula (III)

or a PEA having a chemical formula described by structural formula (IV):

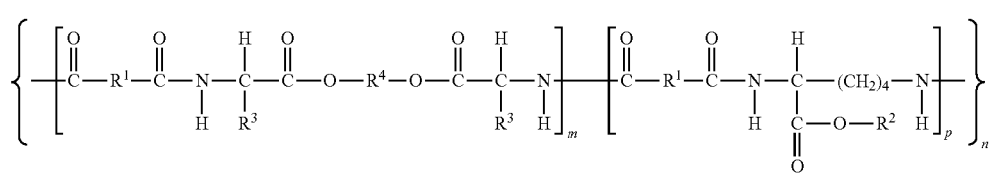

Formula (IV)

polymer carrier layer with an effective amount of at least one bioactive agent dispersed therein and an optional coating layer of a biodegradable biocompatible polymer for controlled release of the bioactive agent in situ. The biodegradable, biocompatible polymer carrier layer includes at least one or a blend of the following: a PEA having a chemical formula described by structural formula (I),

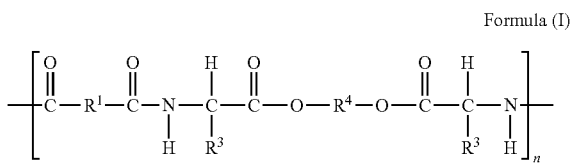

Formula (I)

wherein n ranges from about 5 to about 150; $R^1$ is independently selected from residues of α,ω-bis(4-carboxyphenoxy) ($C_1$-$C_8$) alkane, 3,3'-(alkanedioyldioxy)dicinnamic acid or 4,4'-(alkanedioyldioxy)dicinnamic acid, residues of α,ω-alkylene dicarboxylates of formula (III), ($C_2$-$C_{20}$) alkylene, ($C_2$-$C_{20}$) alkenylene and combinations thereof; wherein $R^5$ and $R^6$ in Formula (III) are independently selected from ($C_2$-$C_{12}$) alkylene or ($C_2$-$C_{12}$) alkenylene; the $R^3$s in individual n monomers are independently selected from the group consisting of hydrogen, ($C_1$-$C_6$) alkyl, ($C_2$-$C_6$) alkenyl, ($C_6$-$C_{10}$) aryl ($C_1$-$C_6$) alkyl and —($CH_2$)$_2$S($CH_3$); and $R^4$ is independently selected from the group consisting of ($C_2$-$C_{20}$) alkylene, ($C_2$-$C_{20}$) alkenylene, ($C_2$-$C_8$) alkyloxy ($C_2$-$C_{20}$) alkylene, bicyclic-fragments of 1,4:3,6-dianhydrohexitols of structural formula (II), and combinations thereof;

wherein n ranges from about 5 to about 150, m ranges about 0.1 to 0.9: p ranges from about 0.9 to 0.1; wherein $R^1$ is independently selected from residues of α,ω-bis(4-carboxyphenoxy) ($C_1$-$C_8$) alkane, 3,3'-(alkanedioyldioxy)dicinnamic acid or 4,4'-(alkanedioyldioxy)dicinnamic acid, residues of α,ω-alkylene dicarboxylates of formula (III), ($C_2$-$C_{20}$) alkylene, ($C_2$-$C_{20}$) alkenylene, and combinations thereof, wherein $R^5$ and $R^6$ in Formula (III) are independently selected from ($C_2$-$C_{12}$) alkylene or ($C_2$-$C_{12}$) alkenylene; each $R^2$ is independently hydrogen, ($C_1$-$C_{12}$) alkyl, ($C_2$-$C_8$) alkyloxy ($C_2$-$C_{20}$) alkyl, ($C_6$-$C_{10}$) aryl or a protecting group; the $R^3$s in individual m monomers are independently selected from the group consisting of hydrogen, ($C_1$-$C_6$) alkyl, ($C_2$-$C_6$) alkenyl, ($C_6$-$C_{10}$) aryl ($C_1$-$C_6$) alkyl and —($CH_2$)$_2$S($CH_3$); and $R^4$ is independently selected from the group consisting of ($C_2$-$C_{20}$) alkylene, ($C_2$-$C_{20}$) alkenylene, ($C_2$-$C_8$) alkyloxy ($C_2$-$C_{20}$) alkylene, bicyclic-fragments of 1,4:3,6-dianhydrohexitols of structural formula (II), and combinations thereof, and $R^7$ is independently ($C_1$-$C_{20}$) alkyl or ($C_2$-$C_{20}$) alkenyl;

a PEUR) having a chemical formula described by structural formula (V),

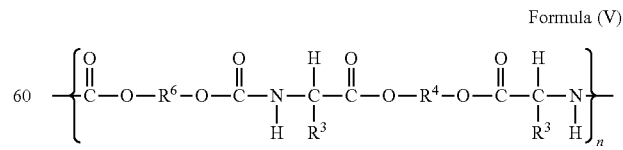

Formula (V)

and wherein n ranges from about 5 to about 150; wherein the $R^3$s within an individual n monomer are independently selected from the group consisting of hydrogen, ($C_1$-$C_6$) alkyl, ($C_2$-$C_6$) alkenyl, ($C_6$-$C_{10}$) aryl($C_1$-$C_6$) alkyl and —(CH$_2$)$_2$S(CH$_3$); R$^4$ and R$^6$ is selected from the group consisting of (C$_2$-C$_{20}$) alkylene, (C$_2$-C$_{20}$) alkenylene or (C$_2$-C$_8$) alkyloxy, and bicyclic-fragments of 1,4:3,6-dianhydrohexitols of structural formula (II, and combinations thereof;

or a PEUR having a chemical structure described by general structural formula (VI),

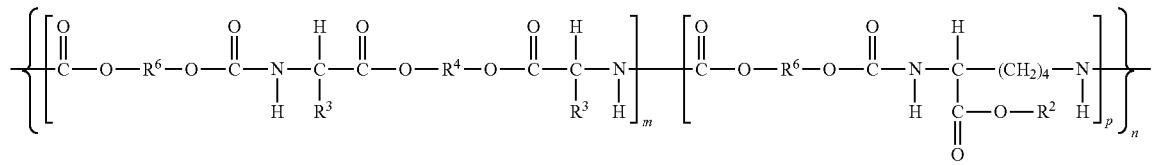

Formula (VI)

wherein n ranges from about 5 to about 150, m ranges about 0.1 to about 0.9: p ranges from about 0.9 to about 0.1; R$^2$ is independently hydrogen, (C$_1$-C$_{12}$) alkyl, (C$_2$-C$_8$) alkyloxy (C$_2$-C$_{20}$) alkyl, (C$_6$-C$_{10}$) aryl or a protecting group; the R$^3$s within an individual m monomer are independently selected from the group consisting of hydrogen, (C$_1$-C$_6$) alkyl, (C$_2$-C$_6$) alkenyl, (C$_6$-C$_{10}$) aryl (C$_1$-C$_6$) alkyl and —(CH$_2$)$_2$S(CH$_3$); R$^4$ and R$^6$ is independently selected from (C$_2$-C$_{20}$) alkylene, (C$_2$-C$_{20}$) alkenylene or (C$_2$-C$_8$) alkyloxy, bicyclic-fragments of 1,4:3,6-dianhydrohexitols of structural formula (II), and combinations thereof, and R$^7$ is independently (C$_1$-C$_{20}$) alkyl or (C$_2$-C$_{20}$) alkenyl, for example, (C$_3$-C$_6$) alkyl or (C$_3$-C$_6$) alkenyl;

or a PEU having a chemical formula described by structural formula (VII),

Formula (VII)

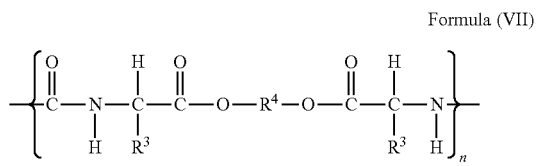

wherein n is about 10 to about 150; the R$^3$s within an individual n monomer are independently selected from hydrogen, (C$_1$-C$_6$) alkyl, (C$_2$-C$_6$) alkenyl, (C$_6$-C$_{10}$) aryl (C$_1$-C$_6$)alkyl and —(CH$_2$)$_2$S(CH$_3$); R$^4$ is independently selected from (C$_2$-C$_{20}$) alkylene, (C$_2$-C$_{20}$) alkenylene, (C$_2$-C$_8$) alkyloxy (C$_2$-C$_{20}$) alkylene; or a bicyclic-fragment of a 1,4:3,6-dianhydrohexitol of structural formula (II) and combinations thereof;

or a PEU having a chemical formula described by structural formula (VIII),

C$_{10}$) aryl or a protecting group; and the R$^3$s within an individual m monomer are independently selected from hydrogen, (C$_1$-C$_6$) alkyl, (C$_2$-C$_6$) alkenyl, (C$_6$-C$_{10}$) aryl (C$_1$-C$_6$)alkyl and —(CH$_2$)$_2$S(CH$_3$); R$^4$ is independently selected from (C$_2$-C$_{20}$) alkylene, (C$_2$-C$_{20}$) alkenylene, (C$_2$-C$_8$) alkyloxy (C$_2$-C$_{20}$) alkylene; or a bicyclic-fragment of a 1,4:3,6-dianhydrohexitol of structural formula (II), or a combination thereof, and R$^7$ is independently (C$_1$-C$_{20}$) alkyl or (C$_2$-C$_{20}$) alkenyl.

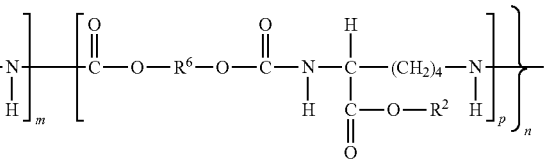

In another embodiment, the invention provides methods for delivering at least one bioactive agent at a controlled rate to an interior body site by implanting into the interior body site an invention solid polymer delivery composition so that the composition will biodegrade to release an effective amount of the at least one bioactive agent into the surrounding tissue at a controlled rate.

In yet another embodiment, the invention provides methods for making a solid polymer delivery composition for controlled release of a bioactive agent by casting or spraying onto a solid substrate the following polymer layers:

i) a carrier layer comprising a liquid dispersion or solution in a first solvent of at least one bioactive agent and a biodegradable, biocompatible polymer;

ii) a coating layer of a liquid solution in a second solvent of a biodegradable, biocompatible polymer; and iii) a barrier layer intermediate between the carrier layer and the coating layer, the barrier layer being a liquid solution of a polymer or copolymer that is insoluble in the first and second solvents, but dissolves under physiological conditions. Each layer is dried before spraying or casting on the next later. The biodegradable biocompatible polymer has a chemical formula described by structural formulas (I and IV-VIII) herein.

In still another embodiment, the invention provides methods for making a solid polymer delivery composition for controlled release of a bioactive agent wherein the composition has a thickness of about 0.1 mm to about 2.5 mm. In this embodiment, a carrier layer comprising a liquid solution in a first solvent of at least one bioactive agent and a biodegradable, biocompatible polymer is sprayed onto a solid substrate and dried. Then at least one coating layer of a liquid solution Formula (VIII)

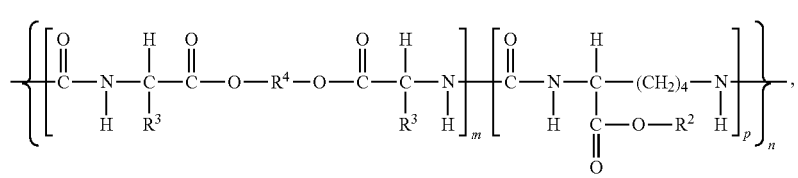 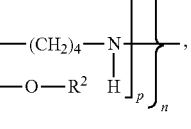

wherein m is about 0.1 to about 1.0; p is about 0.9 to about 0.1; n is about 10 to about 150; each R$^2$ is independently hydrogen, (C$_1$-C$_{12}$) alkyl, (C$_2$-C$_8$) alkyloxy (C$_2$-C$_{20}$) alkyl, (C$_6$- of a biodegradable, biocompatible polymer in the same solvent or in a second solvent is sprayed atop the carrier layer The biodegradable biocompatible polymer of carrier layer and, optionally of the coating layer, has a chemical formula described by structural formulas (I and IV-VIII) herein.

A BRIEF DESCRIPTION OF THE FIGURES

Figure 3:
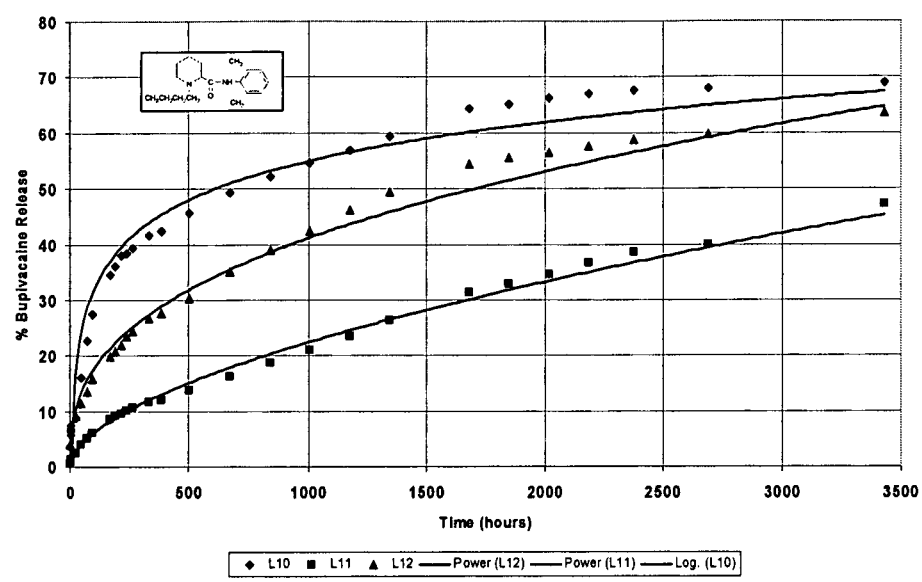

FIG. 3 is a plot from a UV spectrophotometer at 210 nm showing elution of bupivacaine from invention solid polymer delivery compositions as cumulative percent drug released during over 3500 hours. The top curve (-♦-) represents the release of bupivacaine (30% w/w) from a single carrier layer only. The middle curve (-▼-) represents the release of bupivacaine from the same carrier layer covered with a PEA coating layer. The bottom curve (-■-) represents the drug release from the same carrier layer coated first with a PVA barrier layer and then with a PEA top coating.

DETAILED DESCRIPTION OF THE INVENTION

The invention is based on the discovery that biodegradable polymers can be used to create a solid polymer delivery composition for in vivo delivery of bioactive agents dispersed within at a controlled rate. The solid polymer compositions biodegrade by enzymatic action at the surface with no significant breakdown by hydrolysis so as to release the bioactive agent over time at a controlled rate. Due to structural properties of the polymer used, the invention solid polymer delivery composition is implantable, for example in a surgical incision, and can be fabricated to deliver a controlled dosage of bioactive agent(s) at a controlled rate over a prolonged period of time.

As used herein, "bioactive agent" means any molecule, synthetic or natural, that is produced biologically or that affects a biological process in a therapeutic or palliative manner when administered, including without limitation, small molecule drugs, peptides, proteins, DNA, cDNA, RNA, sugars, lipids and whole cells. The bioactive agents are administered by being dispersed in a solid polymer carrier layer in the invention composition, which can have a variety of sizes and structures suitable to meet differing therapeutic goals.

The terms, "biodegradable" and "biocompatible" as used herein to describe the PEA, PEUR and PEU polymers used in the invention solid polymer compositions means the polymer is capable of being broken down into innocuous and bicompatible products in the normal functioning of the body. In one embodiment, the entire solid polymer composition is biodegradable and biocompatible so that the entire composition biodegrades and does not need to be removed at the end of the drug release period. Such PEA, PEUR and PEU polymers have hydrolyzable ester and enzymatically cleavable amide linkages that break down under biological conditions (e.g., in the presence of water and biological enzymes found tissues of mammalian subjects, such as humans. The invention solid polymer delivery compositions, therefore, are also suitable for use in veterinary treatment of a variety of mammalian patients, such as pets (for example, cats, dogs, rabbits, ferrets), farm animals (for example, swine, horses, mules, dairy and meat cattle) and race horses when used as described herein).

Such PEA, PEUR and PEU polymers are typically chain terminated predominantly with amino groups. Optionally, these amino termini can be acetylated or otherwise capped by conjugation to any other suitable acid-containing, biocompatible molecule, to include without restriction organic acids, other polymers and bioinactive molecules. No harmful or irritating breakdown products are formed upon biodegradation of these polymers.

The term "controlled" as used herein to described the release of bioactive agent(s) from invention solid polymer delivery compositions means the solid polymer implant degrades over a desired period of time to provide a smooth and regular (i.e. "controlled") time release profile (e.g., avoiding an initial irregular spike in drug release and providing instead a substantially smooth rate of change of release throughout biodegradation of the invention composition).

The term "dispersed" as used herein to describe the bioactive agents contained in invention solid polymer compositions means the bioactive agent is mixed, dissolved, homogenized, or matrixed within the polymer of at least one carrier layer and also means the bioactive agent can be conjugated to a polymer contained in the invention composition. Two or more bioactive agents may also be dispersed into a polymer layer, such as a carrier layer or a coating layer, or invention compositions may have two or more bioactive agents dispersed into either the same or separate polymer layers therein.

The invention provides a solid polymer delivery composition for implant into an internal body site. The invention comprises a biodegradable, biocompatible polymer comprising at least one or a blend of polymers having a chemical formula described by general structural formulas (I and IV-VIII) as described herein in which is dispersed at least one bioactive agent for release at a controlled rate over a considerable period of time, for example, over a period of three months to about twelve months. The bioactive agent is released in situ as a result of biodegradation of the various polymer layers in the composition. The solid polymer delivery composition may further comprise at least one coating layer of a biodegradable, biocompatible polymer, which may or may not have dispersed therein such a bioactive agent. The purpose of the coating layer of polymer, for example a pure polymer shell, is to slow release of the bioactive agent contained in the composition.

The PEA, PEUR and PEU polymers of formulas (I and IV-VIII) described herein readily absorb water, allowing hydrophilic molecules to readily diffuse therethrough. This characteristic makes such PEA, PEUR and PEU polymers suitable for use as a coating on the invention solid polymer compositions to control release rate of the at least one bioactive agent therefrom.

Rate of release of the at least one bioactive agent from the invention solid polymer delivery compositions can be controlled, not only by selection of the polymers in various layers of the composition, but also by adjusting the coating thickness and density, as well as the number of coating layers contained in the invention composition. Density of the coating layer can be adjusted by adjusting loading of the bioactive agent in the coating layer. For example, when the coating layer contains no bioactive agent, the polymer coating layer is densest, and a bioactive agent from the interior of the composition elutes through the coating layer most slowly. By contrast, when a bioactive agent is dispersed within (i.e. is mixed or "matrixed" with) biodegradable, biocompatible polymer(s) in the coating layer, the coating layer becomes porous once any bioactive agent in the coating layer has eluted out, starting from the outer surface of the coating layer. Once a porous coating layer has formed, a bioactive agent in the carrier layer(s) of the solid composition can elute at an increased rate. The higher the bioactive agent loading in the coating layer, the lower the density of the coating layer and the higher the elution rate. Although loading of bioactive agent in the coating layer can be lower or higher than that in the carrier layer(s), for slowest sustained delivery of a bioactive agent at a controlled rate, the coating layer is a pure polymer shell. There may be multiple coating layers as well as multiple carrier layers in the invention composition.

Accordingly, in one embodiment the invention provides a solid polymer composition for controlled release of a bioactive agent, said composition comprising a carrier layer containing at least one bioactive agent. The bioactive agent is dispersed in a biodegradable, biocompatible polymer comprising at least one or a blend of polymers having a chemical formula described by structural formulas (I and IV-VIII), and at least one coating layer that covers or encapsulates the carrier layer. The coating layer can comprise any biodegradable, biocompatible polymer, such as those described by structural formulas (I and IV-VIII). For convenience in manufacture, the polymer of the coating layer may be the same as the polymer of the carrier layer.

However, it has been discovered that, during manufacture, solvent in the polymer dispersion used to make the coating layer(s) of the invention composition tends to elute the matrixed bioactive agent out of the carrier layer, even though the carrier layer has been dried prior to application of the coating layer. To prevent the solvent used in applying the coating layer from robbing the carrier layer of its load of bioactive agent, the invention composition may further comprise a barrier layer positioned between with a carrier layer and each of one or more coating layers. For example, if the invention composition comprises only one coating layer, the barrier lay is positioned between and is contiguous with the carrier layer and the coating layer. The barrier layer is made using a liquid polymer that will not dissolve in the solvent used in the polymer solution or dispersion that lays down the coating layer in the invention composition, but which barrier layer polymer dissolves in physiologic conditions, for example in the presence of water and physiologic enzymes. Thus, the barrier layer(s), as well as the coating layer(s) of the invention composition, aid in controlling the release rate of the bioactive agent from the carrier layer(s) of the composition.

In certain embodiments, invention solid polymer delivery compositions can have one or multiple sets of the barrier layer and coating layer, with a coating layer being exterior in the final composition to each successive set. Consequently, the carrier layer is sequestered within the protective sets of barrier layer and coating layer. For example, one to ten sets of the barrier layer and coating layer may be present, e.g., one to eight sets, with the number of sets determining the rate of release of the bioactive agent in the carrier layer from the composition. A larger number of sets provides for a slower release rate and a lesser number of sets provides for a faster release rate.

In one embodiment, the sets of barrier layer and coating layer may be aligned in a parallel configuration on either side of the carrier layer in a sandwich structure, with the carrier layer at the center of two sets of barrier layer and coating layer positioned on either side of the carrier layer. In another embodiment, successive outwardly lying layers of the multiple sets of layers encompass all interior layers to form an onionskin structure, as shown schematically in FIG. 1, with the carrier layer sequestered at the center of the composition. Thickness of the carrier layer and concentration of the one or more bioactive agents in the carrier layer determine total dosage of each bioactive agent that the composition can deliver when implanted. After implant or in vitro exposure to physiological conditions (e.g. water and enzymes) the outward most layers of coating and barrier layer begin to biodegrade as encountered by the physiological conditions, and the matrixed bioactive agent(s) elutes from the sequestered carrier layer. As the concentration of bioactive agent in the interior carrier layer diminishes, the surface area of the composition will tend to diminish as well due to biodegradation, with both effects (i.e., decreasing concentration of bioactive agent and decreasing surface area of the composition) tending to slow the rate of release of the bioactive agent in a controlled manner.

In another embodiment, the invention composition comprises multiple sets of carrier and barrier layers arranged in an onionskin structure with a single exterior coating of pure biodegradable, biocompatible polymer, or with alternating layers of barrier layer and coating layer as described above sequestering (e.g. encapsulating) the carrier layer. In this embodiment, water and enzymes from the environment, e.g., tissue surroundings, successively dissolve the outward most coating(s) and barrier layer(s) encountered is the biodegrading composition to elute bioactive agent from successive carrier layers, thereby releasing the matrixed bioactive agent(s). If the concentration of bioactive agent is substantially constant in multiple carrier layers of the onionskin structure, the rate of delivery will diminish in proportion as the surface area of the onionskin structure diminishes. To accomplish a more constant rate of delivery of the matrixed bioactive agent(s), it is recommended in this embodiment to utilize a gradient of concentration of bioactive agent in successive carrier layers in the onionskin structure to be encountered by the tissue surroundings, with a higher concentration being used in inner carrier layers in proportion to the diminishing surface area of the composition. Those skilled in the art will understand that routine principles of fluid dynamics can be used to calculate the theoretical rate of delivery and to obtain a substantially constant rate of delivery as the onionskin structure diminishes in surface area, if desired.

In yet another embodiment, the invention composition comprises an interior carrier layer with additional polymer layers arranged in an onionskin or sandwich structure about the carrier layer. In one alternative, there can be a single exterior coating layer of pure biodegradable, biocompatible polymer formed by spraying a coating layer atop a carrier layer on a substrate, for example, as an aerosol. This structure is favored for compositions having a thickness of 0.1 mm to 2.5 mm in thickness for rapid release of the bioactive agent(s) in the carrier layer. In another alternative, several coating layers extend outwardly from the core carrier layer in an onionskin or sandwich structure. Alternatively still, to achieve a more constant rate of delivery, multiple carrier layers can be employed, provided that each carrier layer is subsequently coated with a coating layer. To effect a gradient of concentration of bioactive molecule(s) in the carrier layer(s) in the onionskin structure, a higher concentration of bioactive molecule(s) is used in inner carrier layers in proportion to the outer carrier layers, such that the rate of release of bioactive molecule(s) can be maintained as the surface area of the composition diminishes during the biodegradation of the invention composition, e.g., when implanted in vivo.

The invention composition typically has a three-dimensional shape, such as a wafer, ball, disc, or cylinder; however, any convenient three dimensional shape can be used. Those of skill in the art of fluid dynamics will understand that choice of the shape of the solid composition will also affect the rate of delivery (e.g., elution) of bioactive agent from the invention composition. Since, the invention composition may be implanted during arthroscopic surgery, for example into an intra-articular or intravertebral space, a cylinder sized to fit down the interior channel of a surgical trochar may be suitably sized for placement during the arthroscopic surgery. In general, however, the invention composition will have a starting surface area in the range from about 1 mm$^2$ to about 90,000 mm$^2$. For example, a disc-shaped solid composition for delivery of a bioactive agent may have a diameter of about 1 mm to about 100 mm and a height of about 0.1 mm to about 20 mm. For implant via a surgical trochar, an invention cylindrical solid composition may have, for example, a diameter of about 1 mm to about 10 mm and a height of about 1 mm to about 50 mm.

To accomplish these goals, yet another embodiment the invention provides methods for making a solid polymer composition for controlled release of a bioactive agent, said methods comprising casting or spraying onto a solid substrate the following polymer layers:

a) at least one carrier layer comprising a liquid solution in a first solvent of at least one bioactive agent and a biodegradable, biocompatible polymer comprising at least one or a blend of polymers having chemical formulas described by structural formulas (I and IV-VIII) as described herein;

b) at least one coating layer of a liquid solution in a second solvent of a biodegradable, biocompatible polymer; and c) at least one barrier layer of a liquid polymer that is insoluble in the second solvent, but dissolves under physiological conditions, wherein the barrier layer lies between the carrier layer and each coating layer. Each layer of the composition is dried before casting or spraying the next layer thereon. A polymer layer cast or sprayed onto the substrate as a liquid dispersion forms a film, for example, a substantially planar body having opposed major surfaces and a thickness between the major surfaces of from about 0.1 millimeters to about 20 millimeters, e.g. 5 millimeters.

Alternatively, for composition constructs having a thickness of about 0.1 to 2.5 mm in thickness, a carrier layer comprising a liquid solution in a first solvent of at least one bioactive agent and a biodegradable, biocompatible polymer, as described herein, is sprayed onto the solid substrate and dried. Then a single coating layer of a liquid solution of a biodegradable, biocompatible polymer in the same solvent or in a second solvent is sprayed atop the carrier layer and dried.

Drying of the various layers can be accomplished using any method known in the art so long as the temperature is not high enough to break down the chemical structure of the various polymers used or that of a bioactive agent dispersed in the carrier layer. Typically, temperatures do not exceed 80° C. For example, the various layers of the composition can be dried in an oven at a temperature of 40° C. to about 50° C. for a period of about 5 hours to about 9 hours, for example, about 7 hours at 50° C., as is illustrated in the Examples herein. In other embodiments the drying time can as long as three weeks, depending upon the structure of the composition and the solvent used.

In one embodiment, the coating layer(s) as well as the carrier layer(s) are applied using a liquid solution of at least one or a blend of polymers having a chemical formula described by structural formulas (I and IV-VIII). Although in no way necessary for practice of the invention, for convenience, it is recommended to use the same combination of solvent and biodegradable, biocompatible polymer of structures (I and IV-VIII) in the coating layer(s) as in the carrier layer(s) of the invention composition. For example, the polymer used in casting or spraying the coating layer(s) can be the same as that used in casting or spraying the carrier layer(s), in which case the first solvent and the second solvent can be identical.

The composition of the barrier layer(s) in the invention composition is an important aspect of the invention. The choice of the polymer used in the barrier layer(s) is determined by the solvent used to form the solution for preparation of the covering layer(s). The purpose of the barrier layer(s) is to prevent uncontrolled solvation of the bioactive agent out of the carrier layer(s) during deposition of the covering layer with which it would otherwise be in contact. Therefore, the polymer for the intermediate barrier layer(s) is selected to be insoluble in solvent used in formation of the covering layer(s). In one embodiment, the barrier layer is a monolayer of the barrier layer polymer in the finished composition. In addition, all polymers used in the various layers of the solid polymer delivery composition are biocompatible and will be re-absorbed by the body through natural enzymatic action. In another embodiment, the coating layer(s) applied are free of bioactive agents and may be referred to herein as a "pure polymer layer".

For example, a polymer that dissolves in ethanol, such as PEA Ac-Bz (a form of the polymer represented in structural formula (I)), can be used in a solution of this solvent (i.e., ethanol) in applying the carrier and coating layers, and a polyvinyl alcohol, which is insoluble in ethanol, can be used to make one or more barrier layers in the composition. In one embodiment, the liquid polymer that forms the barrier layer(s) is applied so as to form a monolayer of the barrier layer polymer, e.g., polyvinyl alcohol.

To further prolong the release period from the invention composition, the composition can have a three-dimensional sandwich structure. The method of making the composition may then be modified by first casting multiple sets of the coating layer and barrier layer onto the substrate, beginning with a coating layer (drying each before deposit of the next) prior to casting the carrier layer in each such set. Then, to form the interior of the sandwich structure, the carrier layer is cast and dried. Finally, in reverse order, multiple sets of the barrier layer and coating layer are cast atop the dried barrier layer. In this way, a coating layer is first and last to be deposited and the composition takes on a sandwich structure, wherein the multiple sets are applied twice to form two external sides of a three-dimensional sandwich structure, with a coating layer being external to both of the two sides of the sandwich structure and with the carrier layer being at the center thereof. Therefore, each composition construct, according to the invention, may either lack a set of the barrier/coating layers or may comprise about one to about ten barrier and coating layer sets (e.g., 1 to about 8 sets of barrier and coating layers).

Figure 1:
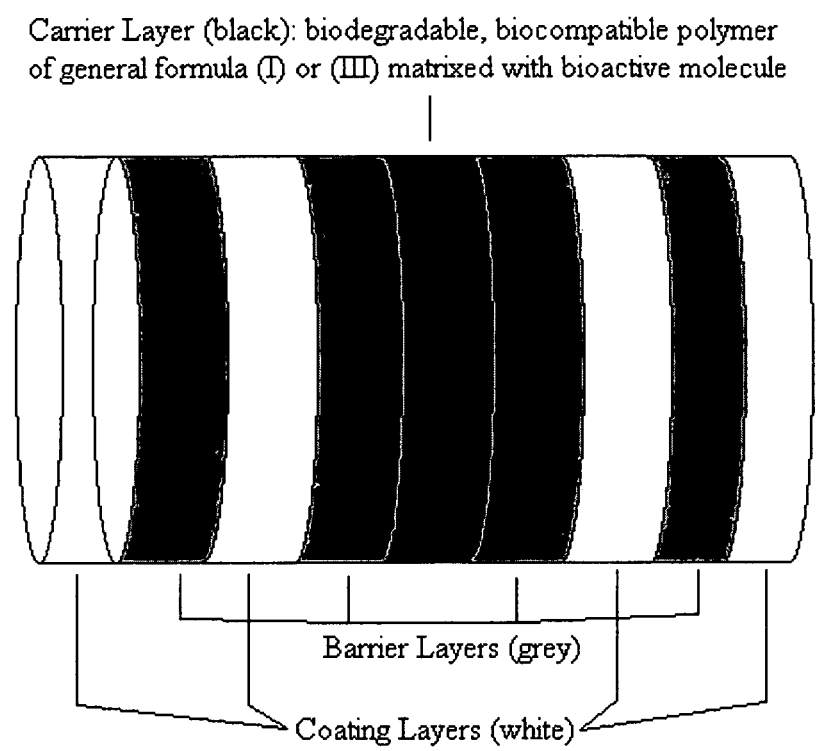
FIG. 1 is a schematic diagram of the invention composition for controlled release of a bioactive agent with the carrier layer (black) sandwiched between two sets of the barrier layer (grey) and coating layer (white). (not drawn to scale)

In a more schematic format, for this embodiment the following procedure can be followed to make a composition having N sets of coating and barrier layers in a sandwich structure, with the carrier layer at the center of the sandwich structure:

1. Cast/spray Nth layer of coating onto substrate and dry,
2. Coat with Nth barrier layer and dry,
3. Cast/spray (N−1)th coating layer and dry,
4. Coat with (N−1)th barrier layer and dry,
5. Repeat steps 3 and 4 as desired.
6. Cast/spray carrier layer containing one or more matrixed bioactive agent (the carrier layer will end up as the innermost layer of the sandwich) and dry.
7. Repeat steps 5 to 1 in the reverse order, ending with a coating layer. Preferably each liquid layer deposited will over run the edge of the previous one to seal the sides of the composition being formed so that elution from the sides of the disc will be controlled as well as from other portions of the surface area. The substrate can be removed from the dried polymer layers at any point in the method of making the invention composition after one or two polymer layers have been cast and dried thereon. The completed composition can be packaged for storage or is ready for immediate use. FIG. 1 is a schematic diagram of such a drug eluting disc formed by the invention method employing a single carrier layer flanked by two sets of barrier layer and coating layer, in a sandwich structure.

Alternatively, if the solvent is not completely removed from the various layers of the composition during the drying steps described above, the composition can be manipulated and compressed to form any of a number of three dimensional shapes, such as by rolling, pleating, folding, and the like, prior to a final drying to substantially remove solvent from the composition. For example, a disc can be rolled up and compressed to form a cylinder. Alternatively, cylinders can be punched with a dye from a sheet of fully dried material formed layer by layer according to the above described methods.

For thinner composition constructs, primarily where the total thickness of the construct does not exceed approximately 2.5 mm, an aerosol of solvated polymer matrixed with bioactive molecule(s) is deposited on a substrate. Alternatively, the carrier layer can be solution cast. This carrier layer is then dried by methodology outlined in c). For the deposition of the coating layer(s) using an aerosol, diffusion of the drug or biologic out of the carrier layer and into the wet coating layer being formed is limited by three factors: 1) concentration of the biodegradable, biocompatible polymer solution is typically as high as possible without forming solids in the air (for example, about 2% to 3%), such that the aerosol is nearly dry upon deposition on the surface, 2) the substrate and/or airspace thereabove are continuously heated (for example, to about 30° C. to 80° C., depending on the polymer and concentration) to promote rapid drying, and 3) a single coat is divided into many "spray cycles." By using "spray cycles," the period of deposition of the aerosol for a single layer of the invention composition is divided into many shorter periods of less than a second in length to several seconds. Each spray period, i.e., "spray cycle, is followed by a short drying period (e.g. 20 to 60 seconds, incorporating continuous heating in each cycle), and such that drying is rapid and residual solvent is minimized for a given coating. Heat can typically be applied continuously, even during the aerosol deposition periods of the spray cycle. Drying of the newly formed coating layer is performed as described herein. Any single coat typically does not exceed approximately 80 μm.

Although in this embodiment of the invention methods of fabrication, migration of the biologic and/or drug into the newly formed coating layer may not be completely eliminated as in embodiments employing the barrier layer, migration is limited to the extent that diffusion of small drug molecules in the final product is slower than in those embodiments containing only a carrier layer. The rate of release of bioactive molecules is thereby controlled.

In yet further embodiments, the invention solid polymer delivery compositions are fabricated as porous solids. A "porous solid", as the term is used herein to describe invention compositions, means compositions that have a ratio of surface area to volume greater than 1:1. As described below, the maximum porosity of an invention solid polymer composition will depend upon its shape and method of fabrication. Any of the various methods for creating pores or "scaffolding" for cell growth in polymers may be used in connection with the present invention. The following examples of methods for fabricating the invention compositions as porous solids are illustrative and not intended to be limiting.

In the first example, the invention composition can be fabricated as a porous solid after the solid polymer delivery composition is formed by cutting pores through the layers of the composition, for example by laser cutting or etching, such as reactive ion etching. For example, short-wavelength UV laser energy is superior to etching for clean-cutting, drilling, and shaping the invention polymer composition. UV laser technology first developed by Massachusetts Institute of Technology (MIT) allows for removal of very fine and measured amounts of material as a plasma plume by "photoablation" with each laser pulse, leaving a cleanly-sculpted pore, or channel. The large size characteristic of the UV excimer laser beam allows it to be separated into multiple beamlets through near-field imaging techniques, so that multiple pores, for example, can be simultaneously bored with each laser pulse. Imaging techniques also allow sub-micron resolution so that nano features can be effectively controlled and shaped. For example, micro-machining of scaffold thickness of 250 microns and channel depth of 200 microns, with pore depth of 50 microns has been achieved using this technique on polycarbonate, polyethylene terephthalate, and polyimide.

In another example, the invention composition is fabricated as a porous solid by adding to the polymer dispersions and solutions used in casting or spraying the various layers of the invention delivery composition a pore-forming substance, such as a gas, or a pore-forming substance (i.e., a porogen) that releases a gas when exposed to heat or moisture. Such pore-forming substances are well known in the art. For example, ammonium bicarbonate salt particles evolve ammonia and carbon dioxide within the solidifying polymer matrix upon solvent evaporation. This method results in a product delivery composition with layers having vacuoles formed therein by gas bubbles. The expansion of pores within the polymer matrix, leads to well interconnected macroporous scaffolds, for example, having mean pore diameters of around 300-400 μm, ideal for high-density ingrowth of cells. (Y. S. Nam et al., *Journal of Biomedical Materials Research Part B: Applied Biomaterials* (2000) 53(1):1-7). Additional techniques known in the art for creating pores in polymers are the combination of solvent-casting with particulate-leaching, and temperature-induced-phase-separation combined with freeze-drying.

In yet another embodiment, each layer of the delivery composition is cast (e.g., spun by electrospinning) onto the substrate or a preceding layer of the composition as an entanglement of fine polymer fibers, such that a polymer mat or pad is formed upon drying of the layer. Electrospinning produces polymer fibers with diameter in the range of 100 nm and even less, from polymer solutions, suspensions of solid particles and emulsions by spinning a droplet in a field of about 1 kV/cm. The electric force results in an electrically charged jet of polymer solution outflowing from a droplet tip. After the jet flows away from the droplet in a nearly straight line, the droplet bends into a complex path and other changes in shape occur, during which electrical forces stretch and thin the droplet by very large ratios. After the solvent evaporates, solidified macro- to nano-fibers are left (D. H. Reneker et al. *Nanotechnology* (1996) 7:216-223).

In still another embodiment, each layer of the delivery composition is placed onto the substrate or a preceding layer of the composition as an entanglement of fine polymer fibers produced from an aerosol, such that a polymer mat or pad is formed. Blown Fiber Deposition (BFD) produces polymer fibers with diameters in the range of 5 μm and greater from polymer solutions. A sprayer is used to form the aerosol and the aerosol droplets converge and dry together in the air to form fibers prior to deposition on a substrate. A funnel or cone is employed about the tip of the nozzle so as to direct the air flow and fibers formed towards the substrate. The pneumatic pressure applied results in dispersion of the polymer solution into an aerosol, and if the pressure is suitably high and if the solution is suitably concentrated enough, fibers form in the air. A forced air heat source is employed to direct warm air at the substrate and facilitate further drying of the newly formed fibers. The nozzle may be of an open design such that solids formed at the tip may be easily cleared and thereby prevent clogging. Optionally, a feed pressure may be applied to the polymer solution feed to aid in preventing the nozzle from clogging.

There are four critical parameters essential for polymer fiber formation from an aerosol of polymer solution, such that fibers form in the air prior to deposition on the substrate. First, a suitably volatile solvent must be selected which dissolves the polymer at high concentrations. Second, the PEA, PEUR or PEU polymer selected must be physically capable of fiber formation. Thirdly, for a given spray device, the atomization pressure used to form the fibers will be higher than the pressures typically used to form uniform coatings with that device. Lastly, for a given spray device, the polymer solution used to produce the fibers will be of higher concentration than what would be used to form uniform coats, as if by painting, for that spray device.

To facilitate uniform deposition of the fibers onto a substrate, a rotating mandrel or drum may be used to collect the fibers. To facilitate release from the substrate of the fibrous mat or pad formed, a substrate which is: 1) relatively non-adhesive to the polymer fibers, 2) low contact area, and 3) does not dissolve in the solvent, is employed.

The following illustrates estimation of the range of porosity that can be anticipated for the above three exemplary modes of fabrication of a rectangular strip of solid polymer, wherein SA=surface area of fabrication; V=volume of fabrication; Vp=volume of polymer solid; Nv=total number of pores; R=average radius of pores; and wherein

*Vv*=total volume of pores is defined by *Nv**4/3 ð $R^3$ Equation 1

*Sv*=total surface area of pores is defined by 4 ð $R^2$ Equation 2; and

*P*—porosity is defined by *Vv/Vp* Equation 3

Porosity of a Standard Rectangular Strip of Solid Film

For a sphere of polymer of radius R, SA/V=3 per unit length, R. For a 1 $cm^3$ solid block of polymer, SA/V=6 $cm^{-1}$, i.e. 6 per unit length. When a 1 $cm^3$ block of solid polymer is pressed into a 1 mm by 1 cm by 10 cm strip, the following holds: SA/V=2.04 or ~2 $mm^{-1}$ and V=1000 $mm^3$=1 $cm^3$ (as for the cube) So, SA=22.2 $cm^2$ and SA/V=~22.2 $cm^{-1}$. For each type of fabrication described above, the surface area to volume ratio of the pores (Sv/Vv) will be calculated in terms of porosity (P), so as to circumvent the necessity of calculating the number of voids, Nv.

Calculations for Equivalent, but Porous Strips or Film

Sv/Vv can be related to SA/V most simply when P=1: For P=1, Vv=Vp=V/2. If the practical approximation that Sv>>SA is made, then SA/V=~2Sv/Vp=k*(Sv/Vp) for constant k=2. When P>1, in each case Sv/Vp increases linearly with P, and SA/V=~kP*(Sv/Vp)

Film with Drilled Holes (Cylindrical Pores)

For each hole drilled, the surface lost=2* ð $R^2$ (on two sides) For each hole drilled, the surface gained is=2ð R*T. Expressed in terms of porosity, for each hole drilled, the surface lost=2* ð $R^2$=2Vv/T, where T is thickness of the film. So, Sv=Nv*[(2ð RT)−(2Vv/T)]=(2ð RT*Vv/ð $R^{2*T}$)−(2Vv/T)=2Vv(1/R−1/T) And, Sv/Vv=2(1/R−1/T) and Sv/Vp=2P(1/R−1/T).

For P=1, Vv=Vp=V/2 and Sv/V=1/R−1/T=~SA/V. Thus, for 200 μm diameter holes (R=0.01 cm) drilled through the above standard strip (T=0.1 cm, V=1 $cm^3$): SA/V=90 $cm^{-1}$=4.5*[(SA/V) for solid strip]. Similarly, for holes of half the above diameter (R=0.005 cm): SA/V=190 $cm^1$=9.5*[(SA/V) for solid strip]

For P>1 the integrity of the essentially two dimensional film, for many applications, may be compromised. However, the theoretical upper limit of porosity can be estimated as follows: Estimating SA/V is linearly proportional to P (from equations above), for 100 μm holes, and a porosity of 90%: SA/V=9*9.5*[(SA/V) solid strip]=85.5*[(SA/V) for solid strip]; which suggests an upper limit of SA/V~100x.

For a Sponge (Formed from Gas Bubbles)

Assuming spherical pores of mean radius R: Sv/Vp=Sv*P/Vv=3*P*Nv*4ð R**2/Nv*4ð R**3=3P/R.

If P=1: Sv/Vp=3/R=~SA/V. If the mean diameter of pores is 200 um (R=0.01 cm), Sv/Vp=3*$10^2$=300 $cm^{-1}$=15*[(SA/V) for a solid strip]. Unlike drilling holes, sponges can be made with very small pores: If mean diameter of pores is 200 nm (R=1*$10^{-5}$ cm), Sv/Vp=3*$10^5$ $cm^{-1}$=~SA/V=15,000*[(SA/V) for solid strip]. Again, Sv/Vp is linearly proportional to porosity, P.

If is P>1: For a porosity of 90%, SA/V=~9*15,000*[(SA/V) for solid strip]; which suggests an upper porosity limit of P~150,000x.

For a Fibrous (Electro-Spun) Weave.

The simplest way to approximate an upper limit of SA/V for this mode of fabrication is to model a square grid, in which the linear dimension 2R of the cubic pores is the same as the thickness of the interleaving polymer sheets. Then, Sv/Vp=3/2R. Furthermore, extending this simplest model to increasing Vv/Vp (i.e. increasing porosity, P), yields Sv/Vp=3P/2R.

If P=1: For 200 nm diameter fibers (R=1*$10^{-5}$ cm), Sv/Vp=3P/2R=(3*1)/2*1*$10^{-5}$ cm or ~SA/V=7,500*[(SA/V) for solid strip].

If P>1: For a porosity of 90%, SA/V=~9*7,500*[(SA/V) for solid strip]; which again suggests an upper limit of P~70,000x.

In summary then, the broadest envisioned range of surface area over volume ratios for drug-eluting films is between 3 and (150,000×20) $cm^{-1}$; i.e. 3 to 3,000,000 (3M) $cm^{-1}$. This range is scaleable; if a very small solid is made with millimeter dimensions, then SA/V can range from 3 to 3M $mm^{-1}$. Thus, in general, the upper limit of the range will be from 3 to 3M per unit length. That is, the most porous solid material envisioned could have a surface area to volume ratio of up to one million times the equivalent solid sphere.

However, those of skill in the art would understand that, in practice, the porosity of the invention polymer solid composition should be considered in light of the strength requirements of the particular application for which the composition is intended. For example, bone substitute fabricated using the invention solid polymer composition would require sufficient strength so that the bone substitute could withstand bodily stress without collapse at the site of implantation. In general, the porosity of human weight-bearing bone varies between 5% and 40%, depending upon the age of the donor and how the measurement was made. Therefore, for use as a bone substitute, the invention solid polymer composition would be selected to have a porosity (v/v) in the range from about 5% to about 40%, for example about 5% to about 30%. Greater porosity would be suitable for non-weight bearing applications.

Any solid substrate, such as a stainless steel, or a PolyTetraFluoroEthylene (PTFE) substrate of any shape, preferably planar, such as a disc, can be used for casting or spraying of the various polymer layers that make up the invention solid polymer delivery compositions. For example in one embodiment, the invention composition is fabricated as a sandwich of polymer layers, which layers are formed by pipetting liquid polymer solutions or dispersions onto a stainless steel disc or poly(tetrafluoroethylene) substrate. The substrate can be left in place during manufacture of the invention composition and then removed any time prior to use.

The Polymers

The biodegradable, biocompatible polymer used at least in the carrier layers of the invention compositions comprises at least one or a blend of the following:

a PEA having a chemical formula described by structural formula (I),

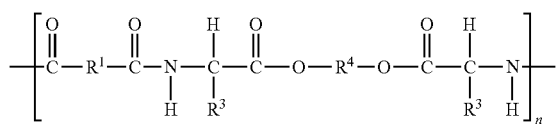

Formula (I)

wherein n ranges from about 5 to about 150; $R^1$ is independently selected from residues of α,ω-bis(4-carboxyphenoxy) ($C_1$-$C_8$) alkane, 3,3'-(alkanedioyldioxy)dicinnamic acid or 4,4'-(alkanedioyldioxy)dicinnamic acid, residues of α,ω-alkylene dicarboxylates of formula (III), ($C_2$-$C_{20}$) alkylene, ($C_2$-$C_{20}$) alkenylene and combinations thereof; wherein $R^5$ and $R^6$ in Formula (III) are independently selected from ($C_2$-$C_{12}$) alkylene or ($C_2$-$C_{12}$) alkenylene; the $R^3$s in individual n monomers are independently selected from the group consisting of hydrogen, ($C_1$-$C_6$) alkyl, ($C_2$-$C_6$) alkenyl, ($C_6$-$C_{10}$) aryl ($C_1$-$C_6$) alkyl and —$(CH_2)_2S(CH_3)$; and $R^4$ is independently selected from the group consisting of ($C_2$-$C_{20}$) alkylene, ($C_2$-$C_{20}$) alkenylene, ($C_2$-$C_8$) alkyloxy ($C_2$-$C_{20}$) alkylene, bicyclic-fragments of 1,4:3,6-dianhydrohexitols of structural formula (II), and combinations thereof;

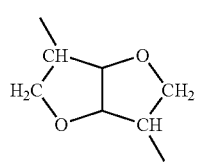

Formula (II)

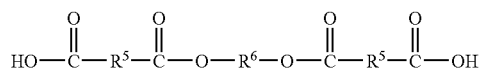

Formula (III)

or a PEA having a chemical formula described by structural formula (IV):

wherein n ranges from about 5 to about 150, m ranges about 0.1 to 0.9: p ranges from about 0.9 to 0.1; wherein $R^1$ is independently selected from residues of α,ω-bis(4-carboxyphenoxy) ($C_1$-$C_8$) alkane, 3,3'-(alkanedioyldioxy)dicinnamic acid or 4,4'-(alkanedioyldioxy)dicinnamic acid, residues of α,ω-alkylene dicarboxylates of formula (III), ($C_2$-$C_{20}$) alkylene, ($C_2$-$C_{20}$) alkenylene, and combinations thereof; wherein $R^5$ and $R^6$ in Formula (III) are independently selected from ($C_2$-$C_{12}$) alkylene or ($C_2$-$C_{12}$) alkenylene; each $R^2$ is independently hydrogen, ($C_1$-$C_{12}$) alkyl, ($C_2$-$C_8$) alkyloxy ($C_2$-$C_{20}$) alkyl, ($C_6$-$C_{10}$) aryl or a protecting group; the $R^3$s in individual m monomers are independently selected from the group consisting of hydrogen, ($C_1$-$C_6$) alkyl, ($C_2$-$C_6$) alkenyl, ($C_6$-$C_{10}$) aryl ($C_1$-$C_6$) alkyl and —$(CH_2)_2S(CH_3)$; and $R^4$ is independently selected from the group consisting of ($C_2$-$C_{20}$) alkylene, ($C_2$-$C_{20}$) alkenylene, ($C_2$-$C_8$) alkyloxy ($C_2$-$C_{20}$) alkylene, bicyclic-fragments of 1,4:3,6-dianhydrohexitols of structural formula (II), and combinations thereof, and $R^7$ is independently ($C_1$-$C_{20}$) alkyl or ($C_2$-$C_{20}$) alkenyl, for example, ($C_3$-$C_6$) alkyl or ($C_3$-$C_6$) alkenyl;

a PEUR) having a chemical formula described by structural formula (V),

Formula (V)

{formula image} and wherein n ranges from about 5 to about 150; wherein the $R^3$s within an individual n monomer are independently selected from the group consisting of hydrogen, ($C_1$-$C_6$) alkyl, ($C_2$-$C_6$) alkenyl, ($C_6$-$C_{10}$) aryl($C_1$-$C_6$) alkyl and —$(CH_2)_2S(CH_3)$; $R^4$ and $R^6$ is selected from the group consisting of ($C_2$-$C_{20}$) alkylene, ($C_2$-$C_{20}$) alkenylene or ($C_2$-$C_8$) alkyloxy, and bicyclic-fragments of 1,4:3,6-dianhydrohexitols of structural formula (II, and combinations thereof;

or a PEUR having a chemical structure described by general structural formula (VI),

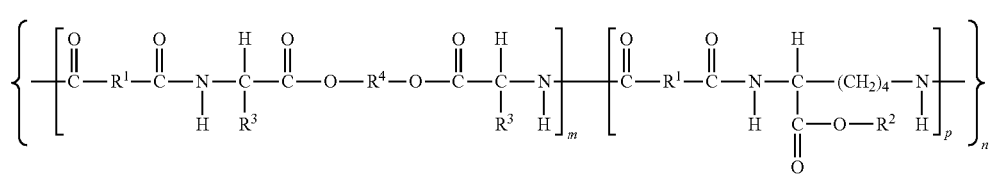

Formula (IV)

Formula (VI)

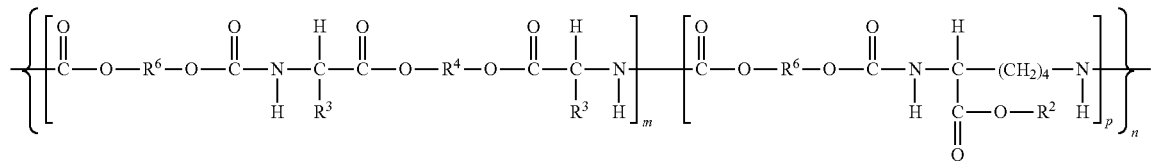

wherein n ranges from about 5 to about 150, m ranges about 0.1 to about 0.9: p ranges from about 0.9 to about 0.1; $R^2$ is independently hydrogen, $(C_1\text{-}C_{12})$ alkyl, $(C_2\text{-}C_8)$ alkyloxy $(C_2\text{-}C_{20})$ alkyl, $(C_6\text{-}C_{10})$ aryl or a protecting group; the $R^3$s within an individual m monomer are independently selected from the group consisting of hydrogen, $(C_1\text{-}C_6)$ alkyl, $(C_2\text{-}C_6)$ alkenyl, $(C_6\text{-}C_{10})$ aryl $(C_1\text{-}C_6)$ alkyl and $\text{—}(CH_2)_2S(CH_3)$; $R^4$ and $R^6$ is independently selected from $(C_2\text{-}C_{20})$ alkylene, $(C_2\text{-}C_{20})$ alkenylene or $(C_2\text{-}C_8)$ alkyloxy, bicyclic-fragments of 1,4:3,6-dianhydrohexitols of structural formula (II), and combinations thereof, and $R^7$ is independently $(C_1\text{-}C_{20})$ alkyl or $(C_2\text{-}C_{20})$ alkenyl, for example, $(C_3\text{-}C_6)$ alkyl or $(C_3\text{-}C_6)$ alkenyl;

or a PEU having a chemical formula described by structural formula (VII),

Formula (VII)

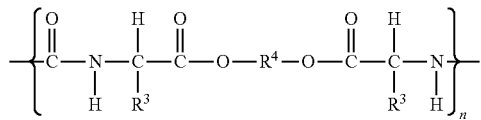

wherein n is about 10 to about 150; the $R^3$s within an individual n monomer are independently selected from hydrogen, $(C_1\text{-}C_6)$ alkyl, $(C_2\text{-}C_6)$ alkenyl, $(C_6\text{-}C_{10})$ aryl $(C_1\text{-}C_6)$alkyl and $\text{—}(CH_2)_2S(CH_3)$; $R^4$ is independently selected from $(C_2\text{-}C_{20})$ alkylene, $(C_2\text{-}C_{20})$ alkenylene, $(C_2\text{-}C_8)$ alkyloxy $(C_2\text{-}C_{20})$ alkylene; or a bicyclic-fragment of a 1,4:3,6-dianhydrohexitol of structural formula (II) and combinations thereof, or a PEU having a chemical formula described by structural formula (VIII), The bicyclic-fragments of the dianhydrohexitols can be derived from sugar alcohols, such as D-glucitol, D-mannitol and L-iditol. $R^6$ may be any combination of 0.1 to 0.9 part of $(C_2\text{-}C_{20})$ alkylene and 0.9 to 0.1 part of $(C_2\text{-}C_{20})$ alkenylene. For example, $R^6$ can be 0.4 to 0.2 part of $(C_2\text{-}C_{20})$ alkenylene to maintain solubility in suitable solvents.

For example in one embodiment of the PEA polymer, at least one $R^1$ is a residue of α,ω-bis(4-carboxyphenoxy) $(C_1\text{-}C_8)$ alkane or 4,4'(alkanedioyldioxy)dicinnamic acid and $R^4$ is a bicyclic-fragment of a 1,4:3,6-dianhydrohexitol of general formula (II). In another alternative, $R^1$ in the PEA polymer is either a residue of α,ω-bis(4-carboxyphenoxy) $(C_1\text{-}C_8)$ alkane, or a residue of 4,4'-(alkanedioyl dioxy) dicinnamic acid, or a combination thereof. In yet another alternative in the PEA polymer, $R^1$ is a residue α,ω-bis(4-carboxyphenoxy) $(C_1\text{-}C_8)$ alkane, such as 1,3-bis(4-carboxyphenoxy)propane (CPP), or 4,4'-(adipoyldioxy)dicinnamic acid, and $R^4$ is a bicyclic-fragment of a 1,4:3,6-dianhydrohexitol of general formula (II), such as 1,4:3,6-dianhydrosorbitol (DAS).

In one alternative in the PEUR polymer, at least one of $R^4$ or $R^6$ is a bicyclic fragment of 1,4:3,6-dianhydrohexitol, such as 1,4:3,6-dianhydrosorbitol (DAS).

In another alternative in the PEU polymer, at least one $R^4$ is a bicyclic fragment of a 1,4:3,6-dianhydrohexitol, such as DAS.

As used herein, to describe the PEA, PEUR and PEU polymers of structural formulas (I and IV-VIII), the terms "amino acid" and "α-amino acid" mean a chemical compound containing an amino group, a carboxyl group and a R group, such as the $R^3$ and $R^5$ groups defined herein. As used herein, the term "biological α-amino acid" means the amino acid(s) used in synthesis are selected from phenylalanine, Formula (VIII)

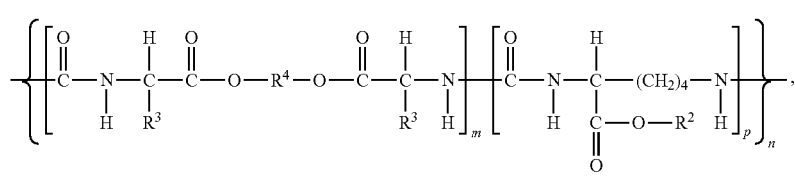

wherein m is about 0.1 to about 1.0; p is about 0.9 to about 0.1; n is about 10 to about 150; each $R^2$ is independently hydrogen, $(C_1\text{-}C_{12})$ alkyl, $(C_2\text{-}C_8)$ alkyloxy $(C_2\text{-}C_{20})$ alkyl, $(C_6\text{-}C_{10})$ aryl or a protecting group; and the $R^3$s within an individual m monomer are independently selected from hydrogen, $(C_1\text{-}C_6)$ alkyl, $(C_2\text{-}C_6)$ alkenyl, $(C_6\text{-}C_{10})$ aryl $(C_1\text{-}C_6)$alkyl and $\text{—}(CH_2)_2S(CH_3)$; $R^4$ is independently selected from $(C_2\text{-}C_{20})$ alkylene, $(C_2\text{-}C_{20})$ alkenylene, $(C_2\text{-}C_8)$ alkyloxy $(C_2\text{-}C_{20})$ alkylene; or a bicyclic-fragment of a 1,4:3,6-dianhydrohexitol of structural formula (II), or a combination thereof, and $R^7$ is independently $(C_1\text{-}C_{20})$ alkyl or $(C_2\text{-}C_{20})$ alkenyl, for example, $(C_3\text{-}C_6)$ alkyl or $(C_3\text{-}C_6)$ alkenyl.

leucine, glycine, alanine, valine, isoleucine, methionine, or a mixture thereof. Additional biological amino acids used in fabrication of co-polymers include lysine and ornithine, but are oriented in the polymer backbone adirectionally (i.e., in a non-biological orientation) such that the carboxyl group of the amino acid is pendent rather than being incorporated into a peptide bond. Additional adirectional amino acids can be incorporated into the invention compositions by varying the $R^7$ group as described herein.

The biodegradable PEA, PEUR and PEU polymers useful in forming the invention compositions may contain multiple different α-amino acids in a single polymer molecule, for example, at least two different amino acids per repeat unit, or a single polymer molecule may contain multiple different amino acids in the polymer molecule, depending upon the size of the molecule.

Suitable protecting groups for use in the PEA, PEUR and PEU polymers include t-butyl or another as is known in the art. Suitable 1,4:3,6-dianhydrohexitols of general formula (II) include those derived from sugar alcohols, such as D-glucitol, D-mannitol, or L-iditol. Dianhydrosorbitol is the presently preferred bicyclic fragment of a 1,4:3,6-dianhydrohexitol for use in the PEA, PEUR and PEU polymers used in fabrication of the invention compositions.

The term "aryl" is used with reference to structural formulae herein to denote a phenyl radical or an ortho-fused bicyclic carbocyclic radical having about nine to ten ring atoms in which at least one ring is aromatic. In certain embodiments, one or more of the ring atoms can be substituted with one or more of nitro, cyano, halo, trifluoromethyl, or trifluoromethoxy. Examples of aryl include, but are not limited to, phenyl, naphthyl, and nitrophenyl.

The term "alkenylene" is used with reference to structural formulae herein to mean a divalent branched or unbranched hydrocarbon chain containing at least one unsaturated bond in the main chain or in a side chain.

In one alternative, at least one of the ax-amino acids used in fabrication of the polymers used in the invention compositions and methods is a biological α-amino acid. For example, when the $R^3$s are $CH_2Ph$, the biological α-amino acid used in synthesis is L-phenylalanine. In alternatives wherein the $R^3$s are $CH_2$—$CH(CH_3)_2$, the polymer contains the biological α-amino acid, L-leucine. By varying the $R^3$s within monomers as described herein, other biological α-amino acids can also be used, e.g., glycine (when the $R^3$s are H), alanine (when the $R^3$s are $CH_3$), valine (when the $R^3$s are $CH(CH_3)_2$), isoleucine (when the $R^3$s are $CH(CH_3)$—$CH_2$—$CH_3$), phenylalanine (when the $R^3$s are $CH_2$—$C_6H_5$), or methionine (when the $R^3$s are —$(CH_2)_2S(CH_3)$, and mixtures thereof. In yet another alternative embodiment, all of the various α-amino acids contained in the polymers used in making the invention solid polymer delivery compositions are biological α-amino acids, as described herein. Biocompatibility of the polymers is optimized when the amino acids used in fabrication of the polymers are biological L-α-amino acids.

Further examples of PEA, PEUR polymers contemplated for use in the practice of the invention and methods of synthesis include those set forth in U.S. Pat. Nos. 5,516,881; 5,610,241; 6,476,204; 6,503,538; in U.S. application Ser. Nos. 10/096,435; 10/101,408; 10/143,572; 10/194,965 and 10/362,848; and in provisional application 60/729,180, filed Oct. 21, 2005.

These biodegradable homopolymers and copolymers preferably have weight average molecular weights ranging from 10,000 to 300,000; these homopolymers and copolymers typically have inherent viscosities at 25° C., determined by standard viscosimetric methods, ranging from 0.3 to 4.0, preferably ranging from 0.5 to 3.5.

The molecular weights and polydispersities herein are determined by gel permeation chromatography (GPC) using polystyrene standards. More particularly, number and weight average molecular weights ($M_n$ and $M_w$) are determined, for example, using a Model 510 gel permeation chromatography (Water Associates, Inc., Milford, Mass.) equipped with a high-pressure liquid chromatographic pump, a Waters 486 UV detector and a Waters 2410 differential refractive index detector. Tetrahydrofuran (THF), N,N-dimethylformamide (DMF) or N,N-dimethylacetamide (DMAc) is used as the eluent (1.0 mL/min). Polystyrene or poly(methyl methacrylate) standards having narrow molecular weight distribution were used for calibration.

Methods for making polymers containing a α-amino acid in the general formula are well known in the art. For example, for the embodiment of the polymer of structural formula (I) wherein $R^4$ is incorporated into an α-amino acid, for polymer synthesis the α-amino acid with pendant $R^3$ can be converted through esterification into a bis-α,ω-diamine, for example, by condensing the α-amino acid containing pendant $R^3$ with a diol HO—$R^4$—OH. As a result, di-ester monomers with reactive α,ω-amino groups are formed. Then, the bis-α,ω-diamine is entered into a polycondensation reaction with a di-acid such as sebacic acid, or bis-activated esters, or bis-acyl chlorides, to obtain the final polymer having both ester and amide bonds (PEA). Alternatively, for example, for polymers of structure (I), instead of the di-acid, an activated di-acid derivative, e.g., bis-para-nitrophenyl diester, can be used as an activated di-acid. Additionally, a bis-di-carbonate, such as bis(p-nitrophenyl)dicarbonate, can be used as the activated species to obtain polymers containing a residue of a di-acid. In the case of PEUR polymers, a final polymer is obtained having both ester and urethane bonds.

More particularly, synthesis of the unsaturated poly(ester-amide)s (UPEAs) useful as biodegradable polymers of the structural formula (I) as disclosed above will now be described,
wherein (a) 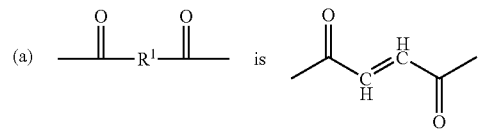 is and/or (b) $R^4$ is —$CH_2$—$CH=CH$—$CH_2$—. In cases where (a) is present and (b) is not present, $R^4$ in (I) is —$C_4H_8$— or —$C_6H_{12}$—. In cases where (a) is not present and (b) is present, $R^1$ in (I) is —$C_4H_8$— or —$C_8H_{16}$—.

The UPEAs can be prepared by solution polycondensation of either (1) di-p-toluene sulfonic acid salt of bis(α-amino acid)di-ester of unsaturated diol and di-p-nitrophenyl ester of saturated dicarboxylic acid or (2) di-p-toluene sulfonic acid salt of bis(α-amino acid)diester of saturated diol and di-nitrophenyl ester of unsaturated dicarboxylic acid or (3) di-p-toluene sulfonic acid salt of bis(α-amino acid)diester of unsaturated diol and di-nitrophenyl ester of unsaturated dicarboxylic acid.

The aryl sulfonic acid salts of diamines are known for use in synthesizing polymers containing amino acid residues. The p-toluene sulfonic acid salts are used instead of the free diamines because the aryl sulfonic salts of bis(α-amino acid) diesters are easily purified through recrystallization and render the amino groups as less reactive ammonium tosylates throughout workup. In the polycondensation reaction, the nucleophilic amino group is readily revealed through the addition of an organic base, such as triethylamine, reacts with bis-electrophilic monomer, so the polymer product is obtained in high yield.

Bis-electrophilic monomers, for example, the di-p-nitrophenyl esters of unsaturated dicarboxylic acid can be synthesized from p-nitrophenyl and unsaturated dicarboxylic acid chloride, e.g., by dissolving triethylamine and p-nitrophenol in acetone and adding unsaturated dicarboxylic acid chloride dropwise with stirring at −78° C. and pouring into water to precipitate product. Suitable acid chlorides included fumaric, maleic, mesaconic, citraconic, glutaconic, itaconic, ethenylbutane dioic and 2-propenyl-butanedioic acid chlorides. For polymers of structure (V) and (VI), bis-p-nitrophenyl dicarbonates of saturated or unsaturated diols are used as the activated monomer. Dicarbonate monomers of general structure (IX) are employed for polymers of structural formula (V) and (VI),

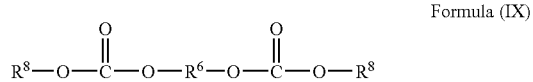

Formula (IX)

wherein each $R^8$ is independently ($C_6$-$C_{10}$) aryl optionally substituted with one or more of nitro, cyano, halo, trifluoromethyl, or trifluoromethoxy; and $R^6$ is independently ($C_2$-$C_{20}$) alkylene or ($C_2$-$C_{20}$) alkyloxy, or ($C_2$-$C_{20}$) alkenylene.

The di-aryl sulfonic acid salts of diesters of α-amino acid and unsaturated diol can be prepared by admixing α-amino acid, e.g., p-aryl sulfonic acid monohydrate and saturated or unsaturated diol in toluene, heating to reflux temperature, until water evolution is minimal, then cooling. The unsaturated diols include, for example, 2-butene-1,3-diol and 1,18-octadec-9-en-diol.

Saturated di-p-nitrophenyl esters of dicarboxylic acid and saturated di-p-toluene sulfonic acid salts of bis-α-amino acid esters can be prepared as described in U.S. Pat. No. 6,503,538 B1.

Synthesis of the unsaturated poly(ester-amide)s (UPEAs) useful as biodegradable polymers of the structural formula (I) as disclosed above will now be described. UPEAs having the structural formula (I) can be made in similar fashion to the compound (VII) of U.S. Pat. No. 6,503,538 B1, except that $R^4$ of (III) of 6,503,538 and/or $R^1$ of (V) of 6,503,538 is ($C_2$-$C_{20}$) alkenylene as described above. The reaction is carried out, for example, by adding dry triethylamine to a mixture of said (III) and (IV) of U.S. Pat. No. 6,503,538 and said (V) of U.S. Pat. No. 6,503,538 in dry N,N-dimethylacetamide, at room temperature, then increasing the temperature to 80° C. and stirring for 16 hours, then cooling the reaction solution to room temperature, diluting with ethanol, pouring into water, separating polymer, washing separated polymer with water, drying to about 30° C. under reduced pressure and then purifying up to negative test on p-nitrophenol and p-toluene sulfonate. A preferred reactant (IV) of U.S. Pat. No. 6,503,538 is p-toluene sulfonic acid salt of Lysine benzyl ester, the benzyl ester protecting group is preferably removed from (II) to confer biodegradability, but it should not be removed by hydrogenolysis as in Example 22 of U.S. Pat. No. 6,503,538 because hydrogenolysis would saturate the desired double bonds; rather the benzyl ester group should be converted to an acid group by a method that would preserve unsaturation. Alternatively, the lysine reactant (IV) of U.S. Pat. No. 6,503, 538 can be protected by a protecting group different from benzyl that can be readily removed in the finished product while preserving unsaturation, e.g., the lysine reactant can be protected with t-butyl (i.e., the reactant can be t-butyl ester of lysine) and the t-butyl can be converted to H while preserving unsaturation by treatment of the product (II) with acid.

A working example of the compound having structural formula (I) is provided by substituting p-toluene sulfonic acid salt of bis(L-phenylalanine) 2-butene-1,4-diester for (III) in Example 1 of U.S. Pat. No. 6,503,538 or by substituting di-p-nitrophenyl fumarate for (V) in Example 1 of U.S. Pat. No. 6,503,538 or by substituting the p-toluene sulfonic acid salt of bis(L-phenylalanine) 2-butene-1,4-diester for III in Example 1 of U.S. Pat. No. 6,503,538 and also substituting bis-p-nitrophenyl fumarate for (V) in Example 1 of U.S. Pat. No. 6,503,538.

In unsaturated compounds having either structural formula (I) or (IV), the following hold. An amino substituted aminoxyl (N-oxide) radical bearing group, e.g., 4-amino TEMPO, can be attached using carbonyldiimidazol, or suitable carbodiimide, as a condensing agent. Bioactive agents, as described herein, can be attached via the double bond functionality.

PEA and PEUR polymers contemplated for use in the practice of the invention can be synthesized by a variety of methods well known in the art. For example, tributyltin (IV) catalysts are commonly used to form polyesters such as poly(ε-caprolactone), poly(glycolide), poly(lactide), and the like. However, it is understood that a wide variety of catalysts can be used to form polymers suitable for use in the practice of the invention.

Such poly(caprolactones) contemplated for use have an exemplary structural formula (X) as follows:

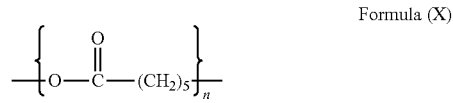

Formula (X)

Poly(glycolides) contemplated for use have an exemplary structural formula (XI) as follows:

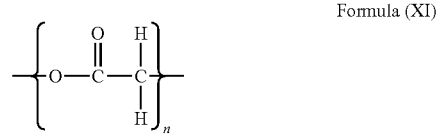

Formula (XI)

Poly(lactides) contemplated for use have an exemplary structural formula (XII) as follows:

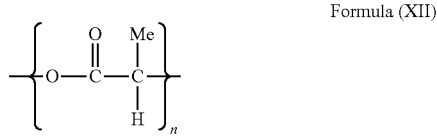

Formula (XII)

An exemplary synthesis of a suitable poly(lactide-co-ε-caprolactone) including an aminoxyl moiety is set forth as follows. The first step involves the copolymerization of lactide and ε-caprolactone in the presence of benzyl alcohol using stannous octoate as the catalyst to form a polymer of structural formula (XIII).

Formula (XIII)

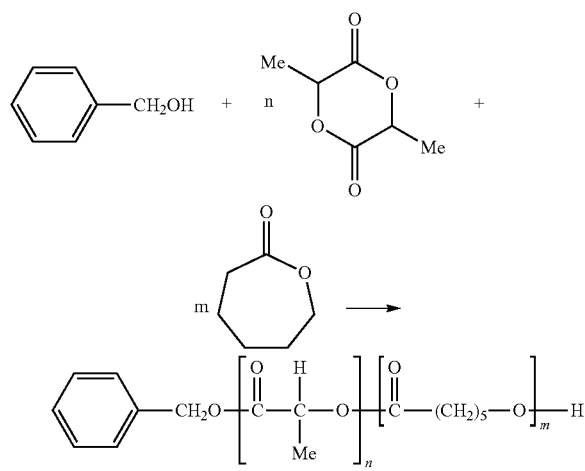

The hydroxy terminated polymer chains can then be capped with maleic anhydride to form polymer chains having structural formula (XIV):

Formula (XIV)

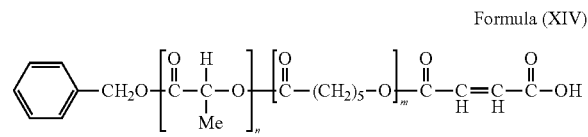

At this point, 4-amino-2,2,6,6-tetramethylpiperidine-1-oxy can be reacted with the carboxylic end group to covalently attach the aminoxyl moiety to the copolymer via the amide bond which results from the reaction between the 4-amino group and the carboxylic acid end group. Alternatively, the maleic acid capped copolymer can be grafted with polyacrylic acid to provide additional carboxylic acid moieties for subsequent attachment of further aminoxyl groups.

In unsaturated compounds having structural formula (VII) for PEU, the following hold: An amino substituted aminoxyl (N-oxide) radical bearing group e.g., 4-amino TEMPO, can be attached using carbonyldiimidazole, or suitable carbodiimide, as a condensing agent. Additional bioactive agents, and the like, as described herein, optionally can be attached via the double bond functionality.

For example, the invention high molecular weight semi-crystalline PEUs having structural formula (VII) can be prepared inter-facially by using phosgene as a bis-electrophilic monomer in a chloroform/water system, as shown in the reaction scheme (2) below:

Scheme 2

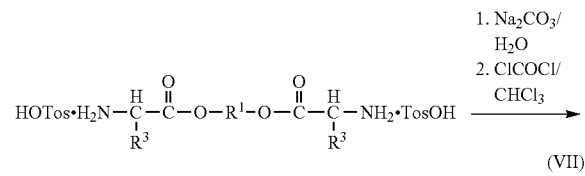

Synthesis of copoly(ester ureas) (PEUs) containing esters of adirectional amino acids, such as L-Lysine esters, and having structural formula (VII) can be carried out by a similar scheme (3):

Scheme 3

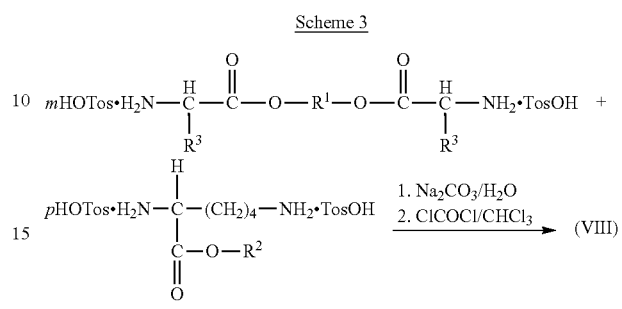

A 20% solution of phosgene (ClCOCl) (highly toxic) in toluene, for example (commercially available (Fluka Chemie, GMBH, Buchs, Switzerland), can be substituted either by diphosgene (trichloromethylchloroformate) or triphosgene (bis(trichloromethyl)carbonate). Less toxic carbonyldiimidazole can be also used as a bis-electrophilic monomer instead of phosgene, di-phosgene, or tri-phosgene.

General Procedure for Synthesis of PEUs

It is necessary to use cooled solutions of monomers to obtain PEUs of high molecular weight. For example, to a suspension of di-p-toluenesulfonic acid salt of bis($\alpha$-amino acid)-$\alpha,\omega$-alkylene diester in 150 mL of water, anhydrous sodium carbonate is added, stirred at room temperature for about 30 minutes and cooled to about 2-0° C., forming a first solution. In parallel, a second solution of phosgene in chloroform is cooled to about 15-10° C. The first solution is placed into a reactor for interfacial polycondensation and the second solution is quickly added at once and stirred briskly for about 15 min. Then the chloroform layer can be separated, dried over anhydrous $Na_2SO_4$, and filtered. The obtained solution can be stored for further use.

All the exemplary PEU polymers fabricated were obtained as solutions in chloroform and these solutions are stable during storage. However, some polymers, for example, 1-Phe-4, become insoluble in chloroform after separation. To overcome this problem, polymers can be separated from chloroform solution by casting onto a smooth hydrophobic surface and allowing chloroform to evaporate to dryness. No further purification of obtained PEUs is needed.

For example, the amide groups at the ends of the polymer chain or a polymer bearing carboxyl groups, such as those of structural formulas (IV, VI and VIII), can readily react with numerous complementary functional groups that can be used to covalently attach a bioactive agent (e.g., an affinity moiety, a peptidic antigen, an insulin molecule, or other macromolecular biologic) to the biodegradable polymer. In another example, an amino moiety in a peptide can readily react with a carboxyl group in these polymers to covalently bond a peptide to the polymer via the resulting amide group. Since the homopolymers of structural formulas (I, V, and VII) contain free functional groups only at the two ends of the polymer chain, whereas the co-polymers of structural formulas (IV, VI and VIII) have a free carboxyl moiety in each adirectional amino acid-based moiety, the co-polymers are suitable for attaching a larger load of bioactive agent than are the homopolymers.

Bioactive Agents

The bioactive agents incorporated into invention solid polymer delivery compositions can have either a therapeutic or palliative activity. Such bioactive agents can have different treatment aims as are known in the art, wherein release of the bioactive agent from the polymer by biodegradation is desirable, for example, by contact with a treatment surface or blood borne cell or factor. Specifically, such bioactive agents can include, but are not limited to, one or more of: proteins, polynucleotides, polypeptides, oligonucleotides, nucleotide analogs, nucleoside analogs, polynucleic acid decoys, therapeutic antibodies, abciximab, antibiotics, analgesics, blood modifiers, anti-platelet agents, anti-coagulation agents, immune suppressive agents, anti-neoplastic agents, such as anti-cancer agents, and anti-cell proliferation agents. The polynucleotide can include deoxyribonucleic acid (DNA), ribonucleic acid (RNA), double stranded DNA, double-stranded RNA, duplex DNA/RNA, antisense polynucleotides, functional RNA or a combination thereof. In one embodiment, the polynucleotide can be RNA. In another embodiment, the polynucleotide can be DNA. In another embodiment, the polynucleotide can be an antisense polynucleotide. In another embodiment, the polynucleotide can be a sense polynucleotide. In another embodiment, the polynucleotide can include at least one nucleotide analog. In another embodiment, the polynucleotide can include a phosphodiester linked 3'-5' and 5'-3' polynucleotide backbone. Alternatively, the polynucleotide can include non-phosphodiester linkages, such as phosphotioate type, phosphoramidate and peptide-nucleotide backbones. In another embodiment, moieties can be linked to the backbone sugars of the polynucleotide. Methods of creating such linkages are well known to those of skill in the art.

The protein can be a growth factor of any of the many families of growth factors that support wound healing and repair. For example, a protein belonging to the transforming growth factor-beta family, such as bone morphogenic protein 12, can be dispersed in the invention polymer composition.

The polynucleotide can be a single-stranded polynucleotide or a double-stranded polynucleotide. The polynucleotide can have any suitable length. Specifically, the polynucleotide can be about 2 to about 5,000 nucleotides in length, inclusive; about 2 to about 1000 nucleotides in length, inclusive; about 2 to about 100 nucleotides in length, inclusive; or about 2 to about 10 nucleotides in length, inclusive. An antisense polynucleotide is typically a polynucleotide that is complimentary to an mRNA, which encodes a target protein. For example, the mRNA can encode a cancer promoting protein i.e., the product of an oncogene. The antisense polynucleotide is complimentary to the single-stranded mRNA and will form a duplex and thereby inhibit expression of the target gene, i.e., will inhibit expression of the oncogene. The antisense polynucleotides of the invention can form a duplex with the mRNA encoding a target protein and will disallow expression of the target protein. A "functional RNA" refers to a ribozyme or other RNA that is not translated.

A "polynucleic acid decoy" is a polynucleic acid which inhibits the activity of a cellular factor upon binding of the cellular factor to the polynucleic acid decoy. The polynucleic acid decoy contains the binding site for the cellular factor. Examples of cellular factors include, but are not limited to, transcription factors, polymerases and ribosomes. An example of a polynucleic acid decoy for use as a transcription factor decoy will be a double-stranded polynucleic acid containing the binding site for the transcription factor. Alternatively, the polynucleic acid decoy for a transcription factor can be a single-stranded nucleic acid that hybridizes to itself to form a snap-back duplex containing the binding site for the target transcription factor. An example of a transcription factor decoy is the E2F decoy. E2F plays a role in transcription of genes that are involved with cell-cycle regulation and that cause cells to proliferate. Controlling E2F allows regulation of cellular proliferation. Examples of other such polynucleic acid decoys and target proteins include, but are not limited to, promoter sequences for inhibiting polymerases and ribosome binding sequences for inhibiting ribosomes. It is understood that the invention includes polynucleic acid decoys constructed to inhibit any target cellular factor.

A "gene therapy agent" refers to an agent that causes expression of a gene product in a target cell through introduction of a gene into the target cell followed by expression of the gene product. An example of such a gene therapy agent would be a genetic construct that causes expression of a protein, such as insulin, when introduced into a cell. Alternatively, a gene therapy agent can decrease expression of a gene in a target cell. An example of such a gene therapy agent would be the introduction of a polynucleic acid segment into a cell that would integrate into a target gene and disrupt expression of the gene. Examples of such agents include viruses and polynucleotides that are able to disrupt a gene through homologous recombination. Methods of introducing and disrupting genes within cells are well known to those of skill in the art.

An oligonucleotide of the invention can have any suitable length. Specifically, the oligonucleotide can be about 2 to about 100 nucleotides in length, inclusive; up to about 20 nucleotides in length, inclusive; or about 15 to about 30 nucleotides in length, inclusive. The oligonucleotide can be single-stranded or double-stranded. In one embodiment, the oligonucleotide can be single-stranded. The oligonucleotide can be DNA or RNA. In one embodiment, the oligonucleotide can be DNA. In one embodiment, the oligonucleotide can be synthesized according to commonly known chemical methods. In another embodiment, the oligonucleotide can be obtained from a commercial supplier. The oligonucleotide can include, but is not limited to, at least one nucleotide analog, such as bromo derivatives, azido derivatives, fluorescent derivatives or a combination thereof. Nucleotide analogs are well known to those of skill in the art. The oligonucleotide can include a chain terminator. The oligonucleotide can also be used, e.g., as a cross-linking reagent or a fluorescent tag. Many common linkages can be employed to couple an oligonucleotide to another moiety, e.g., phosphate, hydroxyl, etc. Additionally, a moiety may be linked to the oligonucleotide through a nucleotide analog incorporated into the oligonucleotide. In another embodiment, the oligonucleotide can include a phosphodiester linked 3'-5' and 5'-3' oligonucleotide backbone. Alternatively, the oligonucleotide can include non-phosphodiester linkages, such as phosphotioate type, phosphoramidate and peptide-nucleotide backbones. In another embodiment, moieties can be linked to the backbone sugars of the oligonucleotide. Methods of creating such linkages are well known to those of skill in the art.

Nucleotide and nucleoside analogues are well known on the art. Examples of such nucleoside analogs include, but are not limited to, Cytovene® (Roche Laboratories), Epivir® (Glaxo Wellcome), Gemzar® (Lilly), Hivid® (Roche Laboratories), Rebetron® (Schering), Videx® (Bristol-Myers Squibb), Zerit® (Bristol-Myers Squibb), and Zovirax® (Glaxo Wellcome). See, *Physician's Desk Reference*, 2005 Edition.

Polypeptides acting as bioactive agents dispersed within the polymers in the invention solid polymer delivery compositions can have any suitable length. Specifically, the polypeptides can be about 2 to about 5,000 amino acids in length, inclusive; about 2 to about 2,000 amino acids in length, inclusive; about 2 to about 1,000 amino acids in length, inclusive; or about 2 to about 100 amino acids in length, inclusive.

The polypeptides can also include "peptide mimetics." Peptide analogs are commonly used in the pharmaceutical industry as non-peptide bioactive agents with properties analogous to those of the template peptide. These types of non-peptide compound are termed "peptide mimetics" or "peptidomimetics." Fauchere, J. (1986) *Adv. Bioactive agent Res.*, 15:29; Veber and Freidinger (1985) TINS p. 392; and Evans et al. (1987) *J. Med. Chem.*, 30:1229; and are usually developed with the aid of computerized molecular modeling. Generally, peptidomimetics are structurally similar to a paradigm polypeptide (i.e., a polypeptide that has a biochemical property or pharmacological activity), but have one or more peptide linkages optionally replaced by a linkage selected from the group consisting of. —$CH_2NH$—, —$CH_2S$—, $CH_2$—$CH_2$—, —CH=CH— (cis and trans), —$COCH_2$—, —$CH(OH)CH_2$—, and —$CH_2SO$—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., *Vega Data* (March 1983), Vol. 1, Issue 3, "Peptide Backbone Modifications" (general review); Morley, J. S., *Trends. Pharm. Sci.*, (1980) pp. 463-468 (general review); Hudson, D. et al., *Int. J. Pept. Prot. Res.*, (1979) 14:177-185 (—$CH_2NH$—, $CH_2CH_2$—); Spatola, A. F. et al., *Life Sci.*, (1986) 38:1243-1249 (—$CH_2$—S—); Harm, M. M., *J. Chem. Soc. Perkin Trans I* (1982) 307-314 (—CH=CH—, cis and trans); Almquist, R. G. et al., *J. Med. Chem.*, (1980) 23:2533 (—$COCH_2$—); Jennings-Whie, C. et al., *Tetrahedron Lett.*, (1982) 23:2533 (—$COCH_2$—); Szelke, M. et al., European Appln., EP 45665 (1982) (—$CH(OH)CH_2$—); Holladay, M. W. et al., *Tetrahedron Lett.*, (1983) 24:4401-4404 (—C(OH) $CH_2$—); and Hruby, V. J., *Life Sci.*, (1982) 31:189-199 (—$CH_2$—S—). Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others.

Additionally, substitution of one or more amino acids within a polypeptide with a D-Lysine in place of L-lysine) may be used to generate more stable polypeptides and polypeptides resistant to endogenous proteases.

In one embodiment, the bioactive agent polypeptide dispersed in the polymer used in the invention compositions can be an antibody. In one embodiment, the antibody can bind to a cell adhesion molecule, such as a cadherin, integrin or selectin. In another embodiment, the antibody can bind to an extracellular matrix molecule, such as collagen, elastin, fibronectin or laminin. In still another embodiment, the antibody can bind to a receptor, such as an adrenergic receptor, B-cell receptor, complement receptor, cholinergic receptor, estrogen receptor, insulin receptor, low-density lipoprotein receptor, growth factor receptor or T-cell receptor. Antibodies attached to polymers (either directly or by a linker) can also bind to platelet aggregation factors (e.g., fibrinogen), cell proliferation factors (e.g., growth factors and cytokines), and blood clotting factors (e.g., fibrinogen). In another embodiment, an antibody can be conjugated to an active agent, such as a toxin. In another embodiment, the antibody can be Abciximab (ReoProR)). Abciximab is a Fab fragment of a chimeric antibody that binds to beta(3) integrins. Abciximab is specific for platelet glycoprotein IIb/IIIa receptors, e.g., on blood cells. Human aortic smooth muscle cells express alpha(v)beta (3) integrins on their surface. Treating beta(3) expressing smooth muscle cells may prohibit adhesion of other cells and decrease cellular migration or proliferation. Abciximab also inhibits aggregation of blood platelets.

Useful anti-platelet or anti-coagulation agents that may be used also include, e.g., Coumadin® (DuPont), Fragmin® (Pharmacia & Upjohn), Heparin® (Wyeth-Ayerst), Lovenox®, Normiflo®, Orgaran® (Organon), Aggrastat® (Merck), Agrylin® (Roberts), Ecotrin® (Smithkline Beecham), Flolan® (Glaxo Wellcome), Halfprin® (Kramer), Integrillin® (COR Therapeutics), Integrillin® (Key), Persantine® (Boehringer Ingelheim), Plavix® (Bristol-Myers Squibb), ReoPro® (Centecor), Ticlid® (Roche), Abbokinase® (Abbott), Activase® (Genentech), Eminase® (Roberts), and Strepase® (Astra). See, *Physician's Desk Reference*, 2005 Edition. Specifically, the anti-platelet or anti-coagulation agent can include trapidil (avantrin), cilostazol, heparin, hirudin, or ilprost.

Trapidil is chemically designated as N,N-dimethyl-5-methyl-[1,2,4]triazolo[1,-5-a]pyrimidin-7-amine.

Cilostazol is chemically designated as 6-[4-(1-cyclohexyl-1H-tetrazol-5-yl)-butoxy]-3,4-dihydro-2(1H)-quinolinone.

Heparin is a glycosaminoglycan with anticoagulant activity; a heterogeneous mixture of variably sulfonated polysaccharide chains composed of repeating units of D-glucosamine and either L-iduronic or D-glucuronic acids.

Hirudin is an anticoagulant protein extracted from leeches, e.g., *Hirudo medicinalis*.

Iloprost is chemically designated as 5-[Hexahydro-5-hydroxy-4-(3-hydroxy-4-methyl-1-octen-6-ynyl)-2(1H)-pentalenylidene]pentanoic acid.

The immune suppressive agent can include, e.g., Azathioprine® (Roxane), BayRho-D® (Bayer Biological), CellCept® (Roche Laboratories), Imuran® (Glaxo Wellcome), MiCRhoGAM® (Ortho-Clinical Diagnostics), Neoran® (Novartis), Orthoclone OKT3® (Ortho Biotech), Prograf® (Fujisawa), PhoGAM® (Ortho-Clinical Diagnostics), Sandimmune® (Novartis), Simulect® (Novartis), and Zenapax® (Roche Laboratories).

Specifically, the immune suppressive agent can include rapamycin or thalidomide. Rapamycin is a triene macrolide isolated from *Streptomyces hygroscopicus*. Thalidomide is chemically designated as 2-(2,6-dioxo-3-piperidinyl)-1H-iso-indole-1,3(2H)-dione.

Anti-cancer or anti-cell proliferation agents that can be incorporated as an bioactive agent into the invention compositions include, e.g., nucleotide and nucleoside analogs, such as 2-chloro-deoxyadenosine, adjunct antineoplastic agents, alkylating agents, nitrogen mustards, nitrosoureas, antibiotics, antimetabolites, hormonal agonists/antagonists, androgens, antiandrogens, antiestrogens, estrogen & nitrogen mustard combinations, gonadotropin releasing hormone (GNRH) analogues, progestrins, immunomodulators, miscellaneous antineoplastics, photosensitizing agents, and skin and mucous membrane agents. See, *Physician's Desk Reference*, 2005 Edition, for specific utilities of such bioactive agents. For example luteinizing hormone-releasing hormone (LHRH), which blocks the production of testosterone and other androgen hormones, is useful in treatment of prostate cancer.

Suitable adjunct antineoplastic agents include Anzemet® (Hoeschst Marion Roussel), Aredia® (Novartis), Didronel® (MGI), Diflucan® (Pfizer), Epogen® (Amgen), Ergamisol® (Janssen), Ethyol® (Alza), Kytril® (SmithKline Beecham), Leucovorin® (Immunex), Leucovorin® (Glaxo Wellcome), Leucovorin® (Astra), Leukine® (Immunex), Marinol® (Roxane), Mesnex® (Bristol-Myers Squibb Oncology/Immunology), Neupogen (Amgen), Procrit® (Ortho Biotech), Salagen® (MGI), Sandostatin® (Novartis), Zinecard® (Pharmacia and Upjohn), Zofran® (Glaxo Wellcome) and Zyloprim® (Glaxo Wellcome).

Suitable miscellaneous alkylating agents include Myleran® (Glaxo Wellcome), Paraplatin® (Bristol-Myers Squibb Oncology/Immunology), Platinol® (Bristol-Myers Squibb Oncology/Immunology) and Thioplex® (Immunex).

Suitable nitrogen mustards include Alkeran® (Glaxo Wellcome), Cytoxan® (Bristol-Myers Squibb Oncology/Immunology), Ifex® (Bristol-Myers Squibb Oncology/Immunology), Leukeran® (Glaxo Wellcome) and Mustargen® (Merck).

Suitable nitrosoureas include BiCNU® (Bristol-Myers Squibb Oncology/Immunology), CeeNU® (Bristol-Myers Squibb Oncology/Immunology), Gliadel® (Rhone-Poulenc Rover) and Zanosar® (Pharmacia and Upjohn).

Suitable antimetabolites include Cytostar-U® (Pharmacia and Upjohn), Fludara® (Berlex), Sterile FUDR® (Roche Laboratories), Leustatin® (Ortho Biotech), Methotrexate® (Immunex), Parinethol® (Glaxo Wellcome), Thioguanine® (Glaxo Wellcome) and Xeloda® (Roche Laboratories).

Suitable androgens include Nilandron® (Hoechst Marion Roussel) and Teslac® (Bristol-Myers Squibb Oncology/Immunology).

Suitable antiandrogens include Casodex® (Zeneca) and Eulexin® (Schering).

Suitable antiestrogens include Arimidex® (Zeneca), Fareston® (Schering), Femara® (Novartis) and Nolvadex® (Zeneca).

Suitable estrogen and nitrogen mustard combinations include Emcyt® (Pharmacia and Upjohn).

Suitable estrogens include Estrace® (Bristol-Myers Squibb) and Estrab® (Solvay).

Suitable gonadotropin releasing hormone (GNRH) analogues include Leupron Depot® (TAP) and Zoladex® (Zenfi).

Suitable progestins include Depo-Provera® (Pharmacia and Upjohn) and Megace® (Bristol-Myers Squibb Oncology/Immunology).

Suitable immunomodulators include Erganisol® (Janssen) and Proleukin® (Chiron Corporation).

Suitable miscellaneous antineoplastics include Camptosar® (Pharmacia and Upjohn), Celestone® (Schering), DTIC-Dome® (Bayer), Elspar® (Merck), Etopophos® (Bristol-Myers Squibb Oncology/Immunology), Etopoxide® (Astra), Gemzar® (Lilly), Hexalen® (U.S. Bioscience), Hycantin® (SmithKline Beecham), Hydrea® (Bristol-Myers Squibb Oncology/Immunology), Hydroxyurea® (Roxane), Intron A® (Schering), Lysodren® (Bristol-Myers Squibb Oncology/Immunology), Navelbine® (Glaxo Wellcome), Oncaspar® (Rhone-Poulenc Rover), Oncovin® (Lilly), Proleukin® (Chiron Corporation), Rituxan® (IDEC), Rituxan® (Genentech), Roferon-A® (Roche Laboratories), Taxol® (paclitaxol/paclitaxel, Bristol-Myers Squibb Oncology/Immunology), Taxotere® (Rhone-Poulenc Rover), TheraCys® (Pasteur Merieux Connaught), Tice BCG® (Organon), Velban® (Lilly), VePesid® (Bristol-Myers Squibb Oncology/Immunology), Vesanoid® (Roche Laboratories) and Vumon® (Bristol-Myers Squibb Oncology/Immunology).

Suitable photosensitizing agents include Photofrin® (Sanofi).

Specifically, useful anti-cancer or anti-cell proliferation agents can include Taxol® (paclitaxel), a nitric oxide-releasing compound, or NicOX (NCX-4016). Taxol® (paclitaxel) is chemically designated as 5β,20-Epoxy-1,2α4,7β,10β,13α-hexahydroxytax-11-en-9-one 4,10-diacetate 2-benzoate 13-ester with (2R,3S)—N-benzoyl-3-phenylisoserine. NCX-4016 is chemically designated as 2-acetoxy-benzoate 2-(nitroxymethyl)-phenyl ester, and is an antithrombotic agent.

Bioactive agents particularly useful for dispersion into and release from the biodegradable polymers used in the invention solid polymer delivery compositions include anti-proliferants, such as rapamycin and any of its analogs or derivatives, paclitaxel or any of its taxene analogs or derivatives, everolimus, Sirolimus (a potent inhibitor of the growth of smooth muscle cells in blood vessels), Everolimus (an immunosuppressant that blocks growth factor-mediated proliferation of hematopoietic and non-hematopoietic cells), tacrolimus (used, e.g., to prevent liver transplant rejection, in Cohn's Disease and ulcerative colitis and as treatment for atomic eczema), or any of its -limus named family of drugs. Also preferred are members of the statin family, such as simvastatin, atorvastatin, fluvastatin, pravastatin, lovastatin, rosuvastatin, geldanamycins, such as 17AAG (17-allylamino-17-demethoxygeldanamycin); Epothilone D and other epothilones, 17-dimethylaminoethylamino-17-demethoxy-geldanamycin and other polyketide inhibitors of heat shock protein 90 (Hsp90), Cilostazol, and the like.

It is appreciated that those skilled in the art understand that the bioactive agent useful in the present invention is the bioactive substance present in any of the bioactive agents or bioactive agents disclosed above. For example, Taxol® is typically available as an injectable, slightly yellow viscous solution. The bioactive agent, however, is a crystalline powder with the chemical name 5β,20-Epoxy-1,2α,4,7β,10β,13α-hexahydroxytax-11-en-9-one 4,10-diacetate 2-benzoate 13-ester with (2R,3S)—N-benzoyl-3-phenylisoserine. *Physician's Desk Reference (PDR)*, Medical Economics Company (Montvale, N.J.), (53rd Ed.), pp. 1059-1067.

A variety of antibiotics are also presently preferred for dispersal in the invention compositions to prevent or control infection. Such antibiotics include many classes, such as aminoglycoside antibiotics or quinolones or beta-lactams, such as cefalosporines, e.g., ciprofloxacin, gentamycin, tobramycin, erythromycin, vancomycin, oxacillin, cloxacillin, methicillin, lincomycin, ampicillin, and colistin. Suitable antibiotics have been described in the literature.

Suitable antimicrobials include, for example, Adriamycin PFS/RDF® (Pharmacia and Upjohn), Blenoxane® (Bristol-Myers Squibb Oncology/Immunology), Cerubidine® (Bedford), Cosmegen® (Merck), DaunoXome® (NeXstar), Doxil® (Sequus), Doxorubicin Hydrochloride® (Astra), Idamycin® PFS (Pharmacia and Upjohn), Mithracin® (Bayer), Mitamycin® (Bristol-Myers Squibb Oncology/Immunology), Nipen® (SuperGen), Novantrone® (Immunex) and Rubex® (Bristol-Myers Squibb Oncology/Immunology). In one embodiment, the peptide can be a glycopeptide. "Glycopeptide" refers to oligopeptide (e.g. heptapeptide) antibiotics, characterized by a multi-ring peptide core optionally substituted with saccharide groups, such as vancomycin.

Examples of glycopeptides included in this category of antimicrobials may be found in "Glycopeptides Classification, Occurrence, and Discovery," by Raymond C. Rao and Louise W. Crandall, ("Bioactive agents and the Pharmaceutical Sciences" Volume 63, edited by Ramakrishnan Nagarajan, published by Marcal Dekker, Inc.). Additional examples of glycopeptides are disclosed in U.S. Pat. Nos. 4,639,433; 4,643,987; 4,497,802; 4,698,327; 5,591,714; 5,840,684; and 5,843,889; in EP 0 802 199; EP 0 801 075; EP 0 667 353; WO 97/28812; WO 97/38702; WO 98/52589; WO 98/52592; and in *J. Amer. Chem. Soc.*, 1996, 118, 13107-13108; *J. Amer. Chem. Soc.*, 1997, 119, 12041-12047; and *J. Amer. Chem. Soc*, 1994, 116, 4573-4590. Representative glycopeptides include those identified as A477, A35512, A40926, A41030, A42867, A47934, A80407, A82846, A83850, A84575, AB-65, Actaplanin, Actinoidin, Ardacin, Avoparcin, Azureomycin, Balhimyein, Chloroorientiein, Chloropolysporin, Decaplanin, -demethylvancomycin, Eremomycin, Galacardin, Helvecardin, Izupeptin, Kibdelin, LL-AM374, Mannopeptin, MM45289, MM47756, MM47761, MM49721, MM47766, MM55260, MM55266, MM55270, MM56597, MM56598, OA-7653, Orenticin, Parvodicin, Ristocetin, Ristomycin, Synmonicin, Teicoplanin, UK-68597, UD-69542, UK-72051, Vancomycin, and the like. The term "glycopeptide" or "glycopeptide antibiotic" as used herein is also intended to include the general class of glycopeptides disclosed above on which the sugar moiety is absent, i.e. the aglycone series of glycopeptides. For example, removal of the disaccharide moiety appended to the phenol on vancomycin by mild hydrolysis gives vancomycin aglycone. Also included within the scope of the term "glycopeptide antibiotics" are synthetic derivatives of the general class of glycopeptides disclosed above, included alkylated and acylated derivatives. Additionally, within the scope of this term are glycopeptides that have been further appended with additional saccharide residues, especially aminoglycosides, in a manner similar to vancosamine.

The term "lipidated glycopeptide" as used herein, refers specifically to those glycopeptide antibiotics which have been synthetically modified to contain a lipid substituent. As used herein, the term "lipid substituent" refers to any substituent that contains 5 or more carbon atoms, preferably, 10 to 40 carbon atoms. The lipid substituent may optionally contain from 1 to 6 heteroatoms selected from halo, oxygen, nitrogen, sulfur, and phosphorous. Lipidated glycopeptide antibiotics are well-known in the art. See, for example, in U.S. Pat. Nos. 5,840,684, 5,843,889, 5,916,873, 5,919,756, 5,952, 310, 5,977,062, 5,977,063, EP 667,353, WO 98/52589, WO 99/56760, WO 00/04044, and WO 00/39156.

Anti-inflammatory agents useful for dispersion in polymers used in invention compositions, depending on the body site into which the invention composition is to be implanted include, e.g. analgesics (e.g., NSAIDS and salicylates), antirheumatic agents, gastrointestinal agents, gout preparations, hormones (glucocorticoids), nasal preparations, ophthalmic preparations, otic preparations (e.g., antibiotic and steroid combinations), respiratory agents, and skin and mucous membrane agents. See, *Physician's Desk Reference*, 2005 Edition. For example, the hormone can be a luteinizing hormone-releasing hormone (LHRH), which blocks the production of testosterone and other androgen hormones and is useful in treatment of prostate cancer. In another example, the anti-inflammatory agent can include dexamethasone, which is chemically designated as (11I, 16I)-9-fluro-11,17,21-trihydroxy-16-methylpregna-1,4-diene-3,20-dione. Alternatively, the anti-inflammatory agent can include sirolimus (rapamycin), which is a triene macrolide antibiotic isolated from *Steptomyces hygroscopicus*.

Bupivacaine is a local anesthetic that blocks the generation and conduction of nerve impulses and therefore is particularly useful for implant at surgical sites and sites of chronic pain. It is commonly used for analgesia by infiltration of surgical incisions. Preemptive use of analgesics (including local anesthetics used to control post-operative pain) i.e. before tissue injury, is recommended to block central sensitization, thus preventing pain or making pain easier to control. Bupivacaine has a longer duration of action than lidocaine, to which it is chemically related—approx. 6-8 hours as opposed to 1-2 hours for lidocaine. Duration of action is affected by the concentration of bupivacaine released from the invention compositions and the volume contained therein. Concentration affects the release rate and hence the time for local anesthesia to occur and the density of the block. Volume released with time determines the area that is infiltrated and therefore anesthetized. Total dose in mg/kg is important in local anesthetic toxicity. As is known in the art, doses up to 225 mg of bupivacaine with adrenaline or 175 mg released without adrenaline may be used for local infiltration for painful musculoskeletal disorders, incisional infiltration for post-operative pain relief, and the like. However, the "effective amount" varies with individual patients, vascularity of the region of the implant site and rate of absorption. Signs of toxicity include central nervous system signs (seizures), and cardiac dysrhythmias progressing to asystole. Bupivacaine toxicity is dose dependent and there is variation between species and age of animals. Rats appear to be more tolerant than larger species (e.g. dogs, sheep, humans), while rabbits are thought to be more sensitive. A serum bupivacaine level of 1.0 µg/mL is generally considered toxic. Dried bupivacaine is available for incorporation into the invention compositions and can be combined with epinephrine (1:200,000), which reduces cutaneous blood flow and therefore prolongs the local anesthetic effects.

In certain embodiments, the polymer/bioactive agent linkage degrades to provide a suitable and effective amount of free bioactive agent.

Any suitable and "effective amount" of bioactive agent can be released over time from the invention compositions and will typically depend on a combination of various factors, e.g., on the particular condition to be treated, the specific polymer used, properties of the bioactive agent such as toxic dosage, and the particular mode of dispersion, for example the type polymer/bioactive agent linkage chosen. In particular, the "effective amount" of the bioactive agent varies with individual patients, vascularity of the region of the implant site and rate of absorption of the bioactive agent. In particular for an antibiotic, the appropriate drug is selected based on bacterial sensitivity and subject allergy and an effective amount depends upon maintaining an adequate serum level; whereas for a cancer treatment, the appropriate drug is selected based on sensitivity of the particular type of cancer to the drug, general health of the subject, and the like, as is known in the art.

Typically, up to about 100% of the bioactive agent can be released from the invention composition by degradation of the composition. Specifically, up to about 90%, up to 75%, up to 50%, or up to 25% of the bioactive agent can be released from the composition. Additional factors that typically affect the "effective amount" of the bioactive agent that is released from the polymer are the nature of the bodily site into which the solid polymer implant is implanted, the shape of the solid polymer implant, the rate of release and the duration of bioactive agent release. The type of polymer and shape of the solid polymer implant can be selected to degrade over a desired period of time to provide a smooth and regular (i.e. "controlled") time release profile (e.g., avoiding an initial spike in drug release and providing instead a substantially smooth rate of change of release throughout biodegradation of the invention composition). Any suitable and effective period of time can be chosen by judicious choice of a combination of the above factors using known principles. Typically, the suitable and effective amount of bioactive agent can be released over a time selected from about twenty-four hours, about seven days, about thirty days, about ninety days, or about 180 days, or longer.

Typically, up to about 100% of the bioactive agent can be released from the invention composition during biodegradation of the implanted composition. Specifically, up to about 90%, up 75%, up to 50%, or up to 25% of the bioactive agent can be released from the polymer/linkeribioactive agent. Factors that typically affect the amount of the bioactive agent released from the polymer include, e.g., the nature and amount of polymer, the nature and amount of bioactive agent, and the nature and amount of additional substances present in the composition.

Polymer Intermixed with Bioactive Agent

A bioactive agent in the carrier or cover layers of the invention compositions described herein can be dispersed in the polymer to be used in making an invention composition by physically intermixing the polymer with solvent and one or more bioactive agents. As used herein, "intermixed" and "matrixed" refers to a polymer as described herein physically mixed with a bioactive agent in a solvent for the polymer, or a polymer as described herein that is physically in contact with, but not conjugated to, a bioactive agent. Upon drying, the solid polymer layer formed by this method may have one or more bioactive agents present on the surface of the polymer layer, partially embedded in the polymer layer, or completely embedded in the polymer layer. Additionally, the composition may include the polymer and a bioactive agent in a homogeneous mixture in a polymer layer, such as carrier layer.

Any suitable amount of polymer and bioactive agent can be employed to provide the dispersion for making a carrier layer or coating layer of the invention composition. The polymer can be present in about 0.1 wt. % to about 99.9 wt. % of the dried layer. Typically, the polymer can be present above about 25 wt. % of the dried layer; above about 50 wt. % of the dried layer; above about 75 wt. % of the dried layer; or above about 90 wt. % of the dried layer. Likewise, the bioactive agent can be present in about 0.1 wt. % to about 99.9 wt. % of the dried layer. Typically, the bioactive agent can be present above about 5 wt. % of the dried layer; above about 10 wt. % of the dried layer; above about 15 wt. % of the dried layer; or above about 20 wt. % of the dried layer in the composition.

Bioactive Agent Conjugated to Polymer

In addition to the bioactive agent being matrixed within or intermixed into the polymer solution used for fabrication of the invention compositions, PEA, PEUR and PEU polymers described by formulas (I and IV-VIII) bear functionalities that allow the option of covalent attachment of bioactive agent(s) to the polymer. In embodiments of the invention wherein the polymer provides free functional groups, prior to combining the components for fabrication of the invention composition, a bioactive agent can be conjugated to the polymer. For example, the amine groups at the ends of the polymer chain or a polymer bearing carboxyl groups, such as those of structural formulas (IV, VI and VIII), can readily react with numerous complementary functional groups that can be used to covalently attach a bioactive agent to the biodegradable polymer. In another example, an amino moiety in a peptide can readily react with a carboxyl group in these polymers to covalently bond a peptide to the polymer via the resulting amide group. Since the homopolymers of structural formulas (I, V, and VII) contain free functional groups only at the two ends of the polymer chain, whereas the co-polymers of structural formulas (IV, VI and VIII) have a free carboxyl group in the adirectional amino acid-based moiety when $R^2$ is H, the co-polymers are suitable for attaching a larger load of bioactive agent than are the homo-polymers.

Accordingly, in one embodiment, the polymers used to make the invention solid polymer delivery compositions as described herein have one or more bioactive agent directly linked to the polymer. The residues of the polymer can be linked to the residues of the one or more bioactive agents either before or after fabrication of the invention compositions. For example, a bioactive agent can be directly linked the polymer in an exterior coating layer of the composition after formation of the composite structure as described herein. Alternatively, one residue of the polymer can be directly linked to one residue of the bioactive agent prior to formation of a carrier layer in the invention composition. The polymer and bioactive agent can each have one open valence. Alternatively, more than one, multiple, or a mixture of bioactive agents having different biologic activities (e.g., therapeutic or palliative) can be directly linked to the polymer. However, since one residue of each bioactive agent is linked to a suitable residue of the polymer, the total number of residues of bioactive agents that can be linked to a polymer corresponds to the number of open valences on the polymer residue.

As used herein a "residue of a bioactive agent" is a radical of such bioactive agent as disclosed herein having one or more open valences. Any synthetically feasible atom or atoms of the bioactive agent can be removed to provide the open valence, provided bioactivity is substantially retained when the radical is attached to a residue of compound of general structures (I) and IV-VIII). Based on the linkage that is desired, those skilled in the art can select suitably functionalized starting materials that can be derived from a bioactive agent using procedures that are known in the art.

The residue of a bioactive agent can be formed employing any suitable reagents and reaction conditions. Suitable reagents and reaction conditions are disclosed, e.g., in *Advanced Organic Chemistry, Part B: Reactions and Synthesis*, Second Edition, Carey and Sundberg (1983); *Advanced Organic Chemistry, Reactions, Mechanisms and Structure*, Second Edition, March (1977); and *Comprehensive Organic Transformations*, Second Edition, Larock (1999).

As used herein, a "residue of a polymer" refers to a radical of a polymer having one or more open valences. Any synthetically feasible atom, atoms, or functional group of the polymer (e.g., on the polymer backbone or pendant group) of the present invention can be removed to provide the open valence, provided bioactivity is substantially retained when the radical is conjugated to a residue of a bioactive agent. Additionally, any synthetically feasible functional group (e.g., carboxyl) can be created on the polymer (e.g., on the polymer backbone or pendant group) to provide the open valence, provided bioactivity is substantially retained when the radical is conjugated to a residue of a bioactive agent. Based on the linkage that is desired, those skilled in the art can select suitably functionalized starting materials that can be derived from the polymer of the present invention using procedures that are known in the art.

As used herein, a "residue of a compound of structural formula (*)" refers to a radical of a compound of polymer formulas (I) and (IV-VIII) as described herein having one or more open valences. For example, the residue of a bioactive agent can be linked to the residue of a compound of structural formula (I) or (IV) through an amide (e.g., —N(R)C(=O)— or —C(=O)N(R)—), ester (e.g., —OC(=O)— or —C(=O)O—), ether (e.g., —O—), amino (e.g., —N(R)—), ketone (e.g., —C(=O)—), thioether (e.g., —S—), sulfinyl (e.g., —S(O)—), sulfonyl (e.g., —S(O)2-), disulfide (e.g., —S—S—), or a direct (e.g., C—C bond) linkage, wherein each R is independently H or (C1-C6) alkyl. Such a linkage can be formed from suitably functionalized polymers and bioactive agents, as described herein, using synthetic procedures that are known in the art.

The number of molecules of bioactive agents that can be linked to the polymer molecule also typically depends upon the molecular weight of the polymer and the equivalents of functional groups incorporated. For example, for a compound of structural formula (I), wherein n is about 5 to about 150, preferably about 5 to about 70, up to about 150 bioactive agent molecules (i.e., residues thereof) can be directly linked to the polymer (i.e., residue thereof) by reacting the bioactive agent with free functional groups of the polymer. In unsaturated polymers, the bioactive agents can also be reacted with double (or triple) bonds in the polymer.

Any suitable size of polymer and bioactive agent can be employed to provide the invention compositions. For example, the polymer can have a size of less than about $1 \times 10^{-4}$ meters, less than about $1 \times 10^{-5}$ meters, less than about $1 \times 10^{-6}$ meters, less than about $1 \times 10^{-7}$ meters, less than about $1 \times 10^{-8}$ meters, or less than about $1 \times 10^{-9}$ meters.

Delivery Characteristics of the Solid Implants

In yet another embodiment, the invention provides methods for delivering at least one bioactive agent at a controlled rate to an interior body site comprising implanting in the interior body site an invention solid polymer delivery composition as described herein and allowing the composition to biodegrade to release the at least one bioactive agent into the surrounding tissue at a controlled rate. In one embodiment, the composition is implanted in a surgical incision at a location selected to deliver the load of bioactive agent(s) to accomplish any therapeutic or palliative goal. For example, the surgical incision can be made arthroscopically and the composition implanted arthroscopically by inserting the composition into the surgical site of interest down a surgical trochar. After placement of the invention composition, the incision can be surgically closed because the polymers in the delivery composition are all biocompatible and will biodegradable over time in situ.

The invention solid polymer delivery composition can degrade to release a suitable and effective amount of the bioactive agent. Any suitable and effective amount of such bioactive agents can be released and will typically depend, e.g., on the specific bioactive agent(s) chosen. Typically, up to about 100% of the bioactive agent(s) can be released from the composition. Specifically, up to about 90%, up to 75%, up to 50%, or up to 25% of the bioactive agent(s) can be released from the composition. Factors that typically affect the amount of the bioactive agent that is released from the composition include, e.g., the chemical structure and amount of polymer (s) used, the chemical structure and amount of bioactive agent (s), and the chemical structure and amount of any additional substances present in the composition.

The composition can degrade over a period of time to provide the suitable and effective amount of bioactive agent. Any suitable and effective period of time can be chosen. For example, the polymer layers of the composition can be selected to release the bioactive agent over about twenty-four hours, about seven days, about thirty days, about ninety days, or about 180 days. Factors that typically affect the length of time over which the bioactive agent is released from the composition include, e.g., the chemical structure and amount of polymer(s) in the layers, the number and combination of the layers, the activity, type and amount of bioactive agent, and the chemical structure and amount of any additional substances present in the composition. Of particular importance in determining the rate and duration of release of the bioactive agent in vivo is the method by which the bioactive agent is dispersed in the composition (i.e., whether by matrixing, mixing into the polymer, and the like, or by conjugation to a functional group in the polymer.

However, it should be noted that bioactive agents conjugated to functional groups contained in the polymers will not undergo timed release from an invention composition at the same rate as the bioactive agents that are matrixed or mixed into the carrier layers of the invention solid polymer delivery compositions. The difference in the timed rate of release from such a biodegradable polymer for any given amount of matrixed and/or covalently bound bioactive agents can be understood with reference to FIG. 2 as follows:

I. Rate of Release of Matrixed Drug from Non-Degradable Polymer (not Shown)

(Phase 1) An initial drug elution rate, r=A, the diffusion rate of the drug out of the polymer, occurs until equilibrium between drug inside and outside of the polymer is reached. At that point all elution would cease if the released drug were not being physiologically removed at rate B, from the vicinity outside of the polymer.

(Phase 2) A steady state elution rate r is achieved that depends upon the relative magnitudes of A and B. If in practice, B is smaller<

(Phase 3) The release rate r is proportional to the amount of drug matrixed within the polymer at any one time. As the drug begins to run out, the diffusion rate A decreases relative to physiological removal rate B of the drug, until the diffusion rate gradually dwindles to zero.

Figure 2:
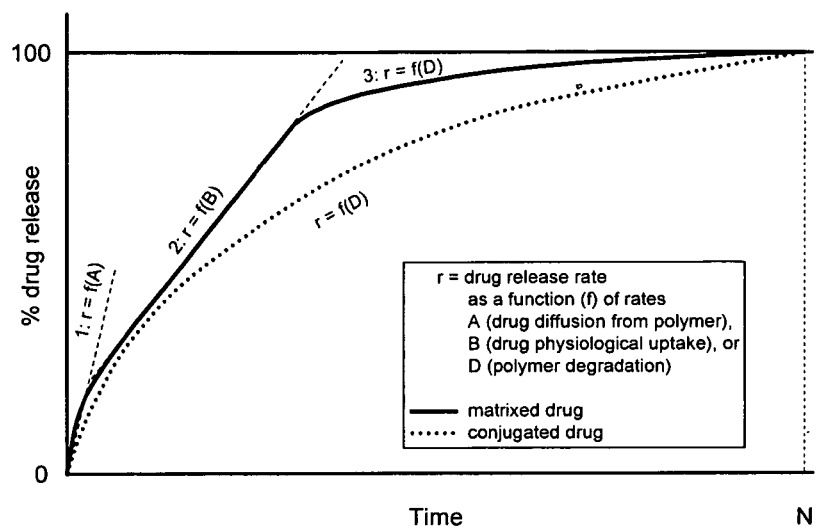
FIG. 2 is a schematic drawing showing release rate for a given amount of dispersed (i.e., "matrixed") and covalently bound bioactive agent from a degradable polymer. Solid line represents dispersed bioactive agent and dotted line represents covalently bound bioactive agent.

II. Rate of Release of Matrixed Drug from Degradable Polymer (FIG. 2)

(Phase 1) An initial drug elution rate, r=A, is as above because for a polymer with degradation rate D, A>>D.

(Phase 2) If, as before we make the assumption that B< is proportional to B for the bulk of the elution, B is independent of A and of D, while A is dependent on D. As the mass of polymer decreases extra drug is forced out. In practice this makes little difference in Phase 2 because, as for Phase 1, A>>D.

(Phase 3). As for Phase 2 above, until, with continuing depletion of drug within the polymer, A approaches D and r becomes dependent upon the relative values of A and D, and ultimately upon D.

Rate of Release from Degradable Polymer with Matrixed Bioactive Agent and Covalently Bound Bioactive Agent FIG. 2).

(1) Dispersed bioactive agent: As above for Phases 1, 2 and 3.

(2) Covalently bound bioactive agents:
(Phase 1) Does not occur.
(Phase 2) D< in turn is proportional to the available surface area (SA) of the polymer. Therefore, drug rate of release r=f(D)=f(SA) (surface erosion).
(Phase 3) Does not occur.

Thus, in use, the elution rate (i.e., rate of delivery) of a bioactive agent matrixed within the invention biodegradable composition by intermixture with the polymer depends, for the bulk of released drug, upon the rate of physiologically removal (B), where B is independent of the polymer degradation rate (D). In contrast, the release of a conjugated bioactive agent depends upon the polymer degradation rate (D) because the polymer degradation rate is much smaller than the rate of physiological removal (B) of the drug (D<<B).

The invention will be further understood with reference to the following examples, which are purely exemplary, and should not be taken as limiting the true scope of the present invention as described in the claims.

EXAMPLES

Example 1

Sample Preparation Procedures
1.1 Preparation of Control Sample.

PEA polymer of structure (I) containing acetylated ends and benzylated COOH groups (PEA-AcBz) was dissolved in 10% EtOH. Bupivacaine (30% of total weight) was added into the solution and the solution was mixed by vortexing and sonication. A pipette was used to drop 20 μL of the bupivacaine-polymer solution onto the surface of a 7/16" stainless steel disc, forming a wet film on the surface of the disc. The disc and film were dried in a 50° C. oven for 7 hours.

1.2 Preparation of a Single Layer Set Coated Sample with Three Total Layers (i.e. Carrier Layer, Barrier Layer and Coating Layer).

A coating of 20 μL of 10% PVA was pipetted onto the control sample described in section 1.1 above and dried in a 50° C. oven for 7 hours. Then a coating of 40 μL of a 10% w/w solution of PEA AcBz in EtOH was applied over the barrier layer and dried in a 50° C. oven for 7 hours.

1.3 Preparation of a Two Layer Set Coated Sample with Five Total Layers (i.e. Carrier Layer, Barrier Layer, Coating Layer, Barrier Layer, Coating Layer)

A coating of 20 μL of 10% w/w of PVA was pipetted onto the single layer set described in section 1.1 above and dried in a 50° C. oven for 7 hours. Then a coating of 40 μL of a 10% w/w solution of PEA AcBz in EtOH was applied over the barrier layer and dried in a 50° C. oven for 7 hours.

Example 2

2.1 Preparation of Control Sample

PEA polymer of structure (I) containing acetylated ends and benzylated COOH groups (PEA-AcBz) was dissolved at approximately 10% in EtOH. Bupivacaine Hydrochloride (33% of total weight) was added into the solution and the solution was mixed by vortexing and sonication. A pipette was used to drop the bupivacaine-polymer solution onto a PTFE substrate, forming a wet film on the surface. The film was air dried initially for a day and then dried in vacuo at 50° C. for two days. The dried sheet of film was approximately 140 μm thick.

2.2 Preparation of a Single Carrier Layer Coated with a Single Coating Layer on One Side PEA polymer of structure (I) containing acetylated ends and benzylated COOH groups (PEA-LD60% AcBz) is dissolved at a concentration of approximately 2% w/w in EtOH. A coating layer was deposited as an aerosol (sprayed) directly onto the dried carrier layer formed in section 2.1 above under a stream of air at a temperature of 70 to 80° C. The carrier layer was oven dried at 80° C. overnight.

2.3 Preparation of a Single Carrier Layer Coated with a Single Coating Layer on Both Sides The carrier layer formed in section 2.1 above with coating layer formed on one side as described in section 2.2 above was then removed from the PTFE substrate. PEA polymer of structure (I) containing acetylated ends and benzylated COOH groups (PEA-AcBz) was dissolved at a concentration of approximately 2% in EtOH. A coating layer was deposited as an aerosol (sprayed) directly onto the dried carrier layer under a stream of air at a temperature of 70 to 80° C. The sheet of coating layer was oven dried at 80° C. overnight. From the dried composite sheet, which was approximately 257 μm thick, 1/8" diameter discs were punched using a dye. The discs weighed 2 mg and consisted of three single layers, i.e. a carrier layer loaded with bioactive bupivacaine with a single coating layer on each side, to form a sandwich structure.

Example 3

Drug Elution

Three discs having a single carrier layer of biodegradable, biocompatible polymer of structure generalized in (I) were prepared by intermixing the polymer with bupivacaine (30% v/w, as in Examples 1 and 2 above. The discs were submerged in phosphate buffered saline (PBS) for drug elution. The drug was detected using a UV spectrophotometer at 210 nm and quantified using a calibration curve. FIG. 3 shows the drug elution as cumulative percent drug released during over 3500 hours. The top curve in FIG. 3 represents the release of bupivacaine from a carrier layer only, as fabricated in section 2.1 of Example 2. The middle curve represents release of bupivacaine from the carrier layer covered with a PEA coating layer. The bottom curve represents release of bupivacaine from the carrier layer, which was covered first with a PVA barrier layer, followed by application of a PEA coating layer.

This data indicates that drug release can be sustained at a controlled rate from an invention solid polymer delivery composition having a carrier layer with bioactive agent dispersed therein. The rate of release can be further sustained by coating a carrier layer directly with a coating layer of polymer, and sustained even further by applying an intermediate barrier layer over the carrier layer before deposition of the coating layer.

Example 4

Fibrous Mats of PEA with 20% Tetracaine Freebase Fabricated by Blown Fiber Deposition This example illustrates fabrication of fibrous, entangled mats of biodegradable PEA fibers from a solution of PEA using the Blown Fiber Deposition (BFD) process. The polymer used is a PEA co-polymer wherein: $R^1=(CH_2)_4$, $R^2=CH_2(C_6H_5)$, $R^3=CH_2CH(CH_3)_2$. $R^4$=is either $(CH_2)_6$ or a fragment of 1,4:3,6 dianhydrosorbitol. PEA and an exemplary drug, Tetracaine freebase, are dissolved in HPLC grade acetone. The ratio of PEA to drug is 4:1 and the total concentration of solids (both PEA and drug) is 15% w/v. The resulting solution is fed into a spray device (a Paasche single action airbrush, Chicago, Ill.) at atmospheric pressure and the atomization pressure is 18 psi using the largest nozzle included for the device. The substrate is PTFE mesh (InterNet Mesh #ET8300), which is mounted about the circumference of a rotating drum (50 rpm). Warm forced air (40° C.) is blown from a heater through a duct directed at the substrate. An entanglement of fine microfibers, 5 μm and larger in diameter, is deposited on the substrate, and builds up to yield a non-woven, entangled mat. The mat is then dried at room temperature in vacuo for five to seven days to remove residual acetone, at which point the fibrous, non-woven mat is removed from the substrate. For a 9/16" disc of the fibrous mat formed as above, the density is approximately 0.5 g/cm$^3$.

Example 5

Synthesis of Porous Thin Sheets of Preformed Micron Polymeric Particles

Previously formed particles of a PEUR polymer (130 mg) were dissolved in 3 ml of acetonitrile. Then a mixture of cottonseed oil and span 80 (4% wt/wt) was added to a 100 ml beaker and the mixture was homogenized by centrifuge (Ultra Turrax T18 basic) (Ika) at 4000 rpm for several minutes. A hydrophilic drug, bupivacaine hydrochloride (50 mg) in 2 ml methanol was mixed with 20 mg of maltose (dissolved in 1 ml methanol) and added to the homogenized polymer particles/cottonseed oil/span 80 solution and the mixture was further homogenized between 6000-1000 rpm for 15 minutes. The solution was then filtered over a 600 mesh stainless steel sheet as substrate and the collected particles were washed on the substrate with hexane to remove remaining cottonseed, oil and span 80, and dried overnight on the substrate to form a polymer sheet. The polymer sheet was then removed from the stainless steel mesh substrate, yielding a white polymer sheet about 100-200 microns thick containing agglomerated particles of from 1-50 microns in diameter.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

Although the invention has been described with reference to the above examples, it will be understood that modifications and variations are encompassed within the spirit and scope of the invention. Accordingly, the invention is limited only by the following claims.

What is claimed is:

1. A method for making a solid polymer composition for controlled release of a bioactive agent comprising:
   a) casting or spraying onto a removable solid substrate the following polymer layers:
      i) a carrier layer comprising a liquid dispersion or solution in a first solvent of at least one bioactive agent and a biodegradable, biocompatible polymer;
      ii) a coating layer of a liquid solution in a second solvent of a biodegradable, biocompatible polymer; and
      iii) a liquid barrier layer intermediate between the carrier layer and the coating layer, wherein the barrier layer is insoluble in the first or second solvent, but dissolves under physiological conditions;
   b) drying each layer before casting or spraying the next layer thereon,
   wherein the biodegradable, biocompatible polymer of a) i) comprises at least one or a blend of poly(ester-amide)s (PEAs) having formula (I) or formula (IV); and
   c) removing the removable solid substrate from the composition prior to use,
   wherein the PEA of formula (I) is:

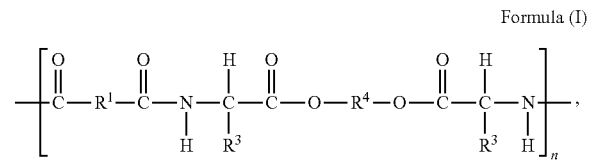

Formula (I)

wherein n ranges from about 5 to about 100;
$R^1$ is independently selected from residues of α,ω-bis(4-carboxyphenoxy)($C_1$-$C_8$)alkane, 3,3'-(alkanedioyldioxy)dicinnamic acid, 4,4'-(alkanedioyldioxy)dicinnamic acid, residues of α,ω-alkylene dicarboxylates of formula (III):

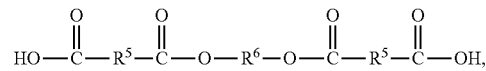

Formula (III)

($C_2$-$C_{20}$)alkylene, ($C_2$-$C_{20}$)alkenylene and combinations thereof;
$R^5$ and $R^6$ are independently selected from ($C_2$-$C_{12}$)alkylene and ($C_1$-$C_{12}$)alkenylene;
the $R^3$s in individual n monomers are independently selected from hydrogen, ($C_1$-$C_6$)alkyl, ($C_2$-$C_6$)alkenyl, ($C_6$-$C_{10}$)aryl($C_1$-$C_6$)alkyl and —($CH_2$)$_2$S($CH_3$); and
$R^4$ is independently selected from ($C_2$-$C_{20}$)alkylene, ($C_2$-$C_{20}$)alkenylene, ($C_2$-$C_8$)alkyloxy ($C_2$-$C_{20}$)alkylene, bicyclic-fragments of 1,4:3,6-dianhydrohexitols of structural formula (II):

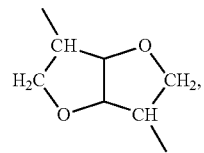

Formula (II)

and combinations thereof; and
wherein the PEA of formula (IV) is:

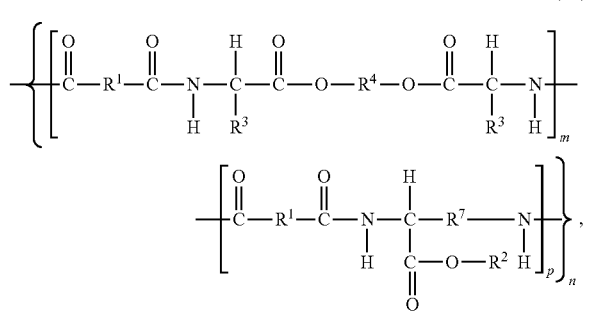

Formula (IV)

wherein n ranges from about 5 to about 150, m ranges about 0.1 to 0.9: p ranges from about 0.9 to 0.1;
$R^1$ is independently selected from residues of α,ω-bis(4-carboxyphenoxy)($C_1$-$C_8$)alkane, 3,3'-(alkanedioyldioxy)dicinnamic acid, 4,4'-(alkanedioyldioxy)dicinnamic acid, residues of α,ω-alkylene dicarboxylates of formula (III), ($C_2$-$C_{20}$)alkylene, ($C_2$-$C_{20}$)alkenylene, and combinations thereof;
$R^5$ and $R^6$ in Formula (III) are independently selected from ($C_2$-$C_{12}$)alkylene and ($C_2$-$C_{12}$)alkenylene;
each $R^2$ is independently selected from hydrogen, ($C_1$-$C_{12}$)alkyl, ($C_2$-$C_8$)alkyloxy($C_2$-$C_{20}$) alkyl, ($C_6$-$C_{10}$)aryl, and a protecting group;
the $R^3$s in individual m monomers are independently selected from hydrogen, ($C_1$-$C_6$) alkyl, ($C_2$-$C_6$)alkenyl, ($C_6$-$C_{10}$)aryl($C_1$-$C_6$)alkyl and —($CH_2$)$_2$S($CH_3$); and
$R^4$ is independently selected from ($C_2$-$C_{20}$)alkylene, ($C_2$-$C_{20}$)alkenylene, ($C_2$-$C_8$)alkyloxy ($C_2$-$C_{20}$)alkylene, bicyclic-fragments of 1,4:3,6-dianhydrohexitols of formula (II), and combinations thereof, and $R^7$ is independently selected from $(C_1-C_{20})$ alkyl and $(C_2-C_{20})$ alkenyl.

2. The method of claim 1, wherein the biodegradable, biocompatible polymer of the coating layer of a) ii) comprises at least one or a blend of PEAs having formula (I) or formula (IV).

3. The method of claim 1, wherein the coating layer is free of bioactive agents.

4. The method of claim 1, wherein the polymer of a) i) is the same as the polymer of a) ii).

5. The method of claim 4, wherein the first solvent and the second solvent are the same.

6. The method of claim 1, wherein the casting is electrospinning and the layers of the composition are formed as a mesh of micro fibers.

7. The method of claim 1, wherein each of the polymer layers further comprises a pore-forming substance that results in the composition product having increased porosity.

8. The method of claim 7, wherein the pore-forming substance forms interconnected macroporous scaffolds in the composition product.

9. The method of claim 1, further comprising repeating a) ii) and a) iii) multiple times to form multiple sets of the barrier layer and the coating layer, with the coating layer of each set being exterior to the barrier layer in the composition.

10. The method of claim 9, wherein the multiple sets are applied twice to form two external sides of a sandwich structure, with a coating layer being exterior to each of the two sides and with the carrier layer being at the center of the sandwich structure.

11. The method of claim 1, wherein two to ten sets of the barrier layer and coating layer are formed.

12. The method of claim 1, wherein two to eight sets of the barrier layer and the coating layer are formed.

13. The method of claim 1, wherein the first solvent is ethanol and the liquid polymer used in a) iii) is polyvinyl alcohol.

14. The method of claim 1, wherein $R^3$ is $CH_2Ph$.

15. The method of claim 1, wherein the barrier layer is free of bioactive agents.

* * * * *